United States Patent
Morse et al.

(10) Patent No.: US 10,319,914 B2
(45) Date of Patent: Jun. 11, 2019

(54) FULLERENE MIXTURES FOR USE IN ORGANIC ELECTRONIC DEVICES

(71) Applicant: MERCK PATENT GMBH, Darmstadt (DE)

(72) Inventors: Graham Morse, Southampton (GB); Jonathan Henry Wilson, Darmstadt (DE); Nicolas Blouin, Darmstadt (DE); Solene Bechu, Nantes (FR)

(73) Assignee: MERCK PATENT GMBH, Darmstadt (DE)

( * ) Notice: Subject to any disclaimer, the term of this patent is extended or adjusted under 35 U.S.C. 154(b) by 0 days.

(21) Appl. No.: 15/508,010

(22) PCT Filed: Aug. 3, 2015

(86) PCT No.: PCT/EP2015/001595
§ 371 (c)(1),
(2) Date: Mar. 1, 2017

(87) PCT Pub. No.: WO2016/034261
PCT Pub. Date: Mar. 10, 2016

(65) Prior Publication Data
US 2017/0294585 A1   Oct. 12, 2017

(30) Foreign Application Priority Data

Sep. 1, 2014   (EP) .................................... 14003011

(51) Int. Cl.
*H01L 51/00*   (2006.01)
*H01L 51/42*   (2006.01)
*C07C 13/62*   (2006.01)

(52) U.S. Cl.
CPC .......... *H01L 51/0047* (2013.01); *C07C 13/62* (2013.01); *H01L 51/0036* (2013.01); *H01L 51/0043* (2013.01); *H01L 51/4253* (2013.01); *C07C 2604/00* (2017.05); *Y02E 10/549* (2013.01)

(58) Field of Classification Search
None
See application file for complete search history.

(56) References Cited

U.S. PATENT DOCUMENTS 8,076,050 B2 * 12/2011 Kronholnn ............. B82Y 10/00
                                                              430/130
2013/0306944 A1   11/2013 Kronholm et al.
2014/0116510 A1   5/2014 Tsao et al.

FOREIGN PATENT DOCUMENTS

| JP | 2005116617 A | 4/2005 |
| JP | 2012201618 A | 10/2012 |
| JP | 2013128001 A | 6/2013 |
| WO | 2011160021 A1 | 12/2011 |
| WO | 2014173484 A1 | 10/2014 |

OTHER PUBLICATIONS

International Search Report for PCT/EP2015/001595 dated Nov. 2, 2015.
Lamparth, I. et al., "Synthesis of [60]Fullerene Derivatives with an Octahedral Addition Pattern," Tetrahedron, 1996, vol. 52, No. 14, pp. 5065-5075.
Lindqvist, C. et al., "Fullerene mixtures enhance the thermal stability of a non-crystalline polymer solar cell blend," Applied Physics Letters, 2014, vol. 104, pp. 153301-1-153301-4.
Kastner, C. et al., "Polymer BHJ Solar Cell Performance Tuning by C60 Fullerene Derivative Alkyl Side-Chain Length," Journal of Polymer Science Part B: Polymer Physics, 2012, vol. 50, pp. 1562-1566.
Lee, Kwang-Hoi et al, "Synthesis and Optical Properties of pi-Conjugated Polymers Composed of Benzo[1,2-b:4,5-b'] dithiophene and Thiophenes Bearing Electron-Deficient Ethenyl Groups in the Side Chains," Macromol. Chem. Phys., 2010, vol. 211, pp. 2490-2496.
Kooistra, F. B. et al., "Increasing the Open Circuit Voltage of Bulk-Heterojunction Solar Cells by Raising the LUMO Level of the Acceptor," Organic Letters, 2007, vol. 9, No. 4, pp. 551-554.
English Abstract of JP-2012201618, Publication Date: Oct. 22, 2012.
English Abstract of JP-2005116617, Publication Date: Apr. 28, 2005.
English Abstract of JP-2013128001, Publication Date: Jun. 27, 2013.

* cited by examiner

*Primary Examiner* — Catherine S Branch
(74) *Attorney, Agent, or Firm* — Millen, White, Zelano and Branigan, P.C.

(57) ABSTRACT

The invention relates to novel mixtures of substituted fullerenes, to their use in organic electronic (OE) devices, especially organic photovoltaic (OPV) devices and organic photodetectors (OPD), and to OE, OPV and OPD devices comprising these fullerene mixtures.

20 Claims, No Drawings

FULLERENE MIXTURES FOR USE IN ORGANIC ELECTRONIC DEVICES

TECHNICAL FIELD

The invention relates to novel mixtures of substituted fullerenes, to their use in organic electronic (OE) devices, especially organic photovoltaic (OPV) devices and organic photodetectors (OPD), and to OE, OPV and OPD devices comprising these fullerene mixtures.

BACKGROUND

The photosensitive layer in an organic photovoltaic (OPV) or an organic photodetector (OPD) device is composed of at least two components, a p-type semiconductor such as a polymer, an oligomer or a defined molecular unit as first component, and a n-type semiconductor such as a fullerene or substituted fullerene, graphene, a metal oxide, or quantum dots as second component. In recent years, the stability of OPV devices has been investigated. The interactions which take place during OPV operation are complicated which generates many pathways for OPV device degradation. One approach to impact the stability of OPV devices is to modify the n-type semiconductor. Recently the approach to using modified n-type semiconductors and n-type semiconductor mixtures has been limited to only a few selected candidates, like PCBM-$C_{60}$.

More recent approaches to stabilizing OPV devices by formulation of n-type semiconductors as promising alternatives to PCBM-$C_{60}$ are limited, for example, to using mixtures of monosubstituted and polysubstituted fullerenes, as disclosed for example in US 2014/0116510 A1, using mixtures of unsubstituted, monosubstituted and polysubstituted fullerenes, as disclosed for example in US 2013/0306944 A1, or using different sizes of fullerenes, as disclosed for example in C. Lindqvist et al., *Appl. Phys. Lett.*, 2014, 104, 153301. However, the physical properties of these mixtures such as solubility, light stability, power conversion efficiency, and thermal stability limit their broad commercial application.

Thus there is still a need for fullerene materials which show good structural organization and film-forming properties, exhibit good electronic properties, especially a high charge carrier mobility, a good processability, especially a high solubility in organic solvents, and high light and thermal stability, and are suitable for use as n-type semiconductors in OE devices, especially in OPV and OPD devices.

It was an aim of the present invention to provide fullerene materials that provide one or more of the above-mentioned advantageous properties. Another aim of the invention was to extend the pool of n-type OSC materials available to the expert. Other aims of the present invention are immediately evident to the expert from the following detailed description.

The inventors of the present invention have found that one or more of the above aims can be achieved by providing mixtures of substituted fullerenes as disclosed and claimed hereinafter.

In particular, the inventors of the present invention have found that, instead of mixing fullerenes having different size or different degree of substitution, providing mixtures of substituted fullerenes with specific variation in the nature of the substituent offer significant unexpected advantages in the stability of OPV devices over other approaches.

SUMMARY

The invention relates to a mixture comprising two or more compounds of formula I, including isomers thereof, (hereinafter referred to as "fullerene mixture"),

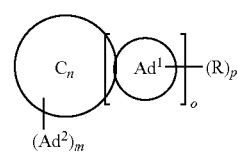

wherein the individual radicals, independently of each other, and on each occurrence identically or differently, have the following meanings $C_n$ a fullerene composed of n carbon atoms, optionally with one or more atoms trapped inside, $Ad^1$ a first adduct selected from formulae 1-8, which is preferably a [6,6]-adduct or [5,6]-adduct to the fullerene

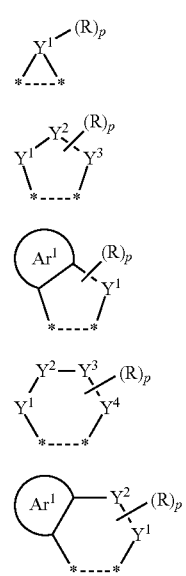

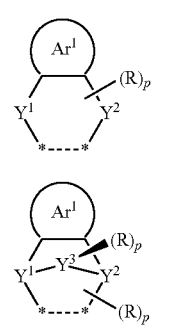

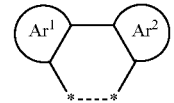

o an integer ≥1 or a non-integer >1,

R halogen, CN, an alkyl group with 1 to 50 C atoms, which is straight-chain, branched or cyclic, and in which one or more $CH_2$ groups are optionally replaced by —O—, —S—, —C(=O)—, —C(=S)—, —C(=O)—O—, —O—C(=O)—, —NR$^o$—, —C(=O)—NR$^o$—, —NR$^o$—C(=O)—, —SiR$^o$R$^{oo}$—, —CF$_2$—, —CR$^o$=CR$^{oo}$—, —CR$^o$=N—, —N=N— or —C≡C— in such a manner that O and/or S atoms are not linked directly to one another, and/or in which one or more H atoms are optionally replaced by F, Cl, Br, I or CN, a saturated or unsaturated, non-aromatic carbo- or heterocyclic group, or an aryl, heteroaryl, aryloxy or heteroaryloxy group, wherein each of the aforementioned groups has 5 to 20 ring atoms, is mono- or polycyclic, does optionally contain fused rings, and is optionally substituted by one or more identical or different groups L, p 0 or an integer ≥1, L halogen, —CN, —NC, —NCO, —NCS, —OCN, —SCN, —C(=O)NR$^o$R$^{oo}$, —C(=O)X$^o$, —C(=O)R$^o$, —NH$_2$, —NR$^o$R$^{oo}$, —SH, —SR$^o$, —SO$_3$H, —SO$_2$R$^o$, —OH, —NO$_2$, —CF$_3$, —SF$_5$, optionally substituted silyl, or carbyl or hydrocarbyl with 1 to 40 C atoms that is optionally substituted and optionally comprises one or more hetero atoms, preferably alkyl, alkoxy, thioalkyl, alkylcarbonyl, alkylcarbonyloxy, alkoxycarbonyl or alkoxycarbonyloxy with 1 to 20 C atoms that is optionally fluorinated, R$^o$, R$^{oo}$ H or alkyl with 1 to 12 C atom, X$^o$ halogen, preferably F, Cl or Br,

* - - - * a linkage to the fullerene, $Y^1, Y^2, Y^3, Y^4$ C, Si, Ge, Sn, N, P, B, Al, Ga, S, O or Se, which can be further substituted by one or more groups L and can posses any bond configuration, $Ar^1, Ar^2$ a double bond, a saturated or unsaturated, non-aromatic carbo- or heterocyclic group, or an aryl, heteroaryl, aryloxy or heteroaryloxy group, wherein each of the aforementioned groups has 5 to 20 ring atoms, is mono- or polycyclic, does optionally contain fused rings, and is optionally substituted by one or more identical or different groups L, $Ad^2$ a second adduct, or a combination of second adducts, appended to the fullerene $C_n$ with any connectivity, m 0, an integer ≥1, or a non-integer >0.

with the provisos that the mixture comprises
a) at least two compounds of formula I differing in the nature of at least one of their adducts $Ad^1$, and/or
b) at least two compounds of formula I differing in the nature of at least one of the substituents R on their adducts $Ad^1$, and/or
c) at least two compounds of formula I differing in the number p of the substituents R on their adducts $Ad^1$.

The invention further relates to a fullerene mixture comprising two or more compounds of formula I as described above and below, and further comprising one or more fullerenes or fullerene derivatives, which are selected from fullerenes of formula I having a different number n of carbon atoms or are selected from fullerenes that are different from formula I.

The invention further relates to the use of a fullerene mixture as described above and below as electron acceptor or n-type semiconductor.

The invention further relates to the use of a fullerene mixture as described above and below as electron acceptor or n-type component in a semiconducting material, organic electronic device or component of an organic electronic device.

The invention further relates to a composition comprising a fullerene mixture as described above and below.

The invention further relates to a composition comprising a fullerene mixture as described above and below, preferably as electron acceptor or n-type component, and further comprising one or more semiconducting compounds, which preferably have electron donor or p-type properties.

The invention further relates to a composition comprising a fullerene mixture as described above and below, and further comprising one or more p-type organic semiconductor compounds, preferably selected from conjugated organic polymers.

The invention further relates to a composition comprising a fullerene mixture as described above and below, and further comprising one or more compounds which are selected from compounds having one or more of a semiconducting, charge transport, hole transport, electron transport, hole blocking, electron blocking, electrically conducting, photoconducting, photoactive and light emitting property.

The invention further relates to the use of a fullerene mixture as described above and below, or a composition comprising it, as semiconducting, charge transport, electrically conducting, photoconducting, photoactive or light emitting material, or in an organic electronic (OE) device, or in a component of such an OE device or in an assembly comprising such an OE device or such a component.

The invention further relates to a semiconducting, charge transport, electrically conducting, photoconducting, photoactive or light emitting material, which comprises a fullerene mixture as described above and below or a composition comprising it as described above and below.

The invention further relates to a formulation comprising a fullerene mixture as described above and below, or a composition or material comprising it as described above and below, and further comprising one or more solvents, preferably selected from organic solvents, very preferably from non-chlorinated organic solvents, most preferably from non-halogenated organic solvents.

The invention further relates to an OE device, or a component thereof, or an assembly comprising it, which is prepared using a formulation as described above and below.

The invention further relates to an OE device, or a component thereof, or an assembly comprising it, which comprises a fullerene mixture as described above and below, or a composition or a material comprising it as described above and below.

The OE device is preferably an optical, electrooptical, electronic, photoactive, electroluminescent or photoluminescent device.

The OE device includes, without limitation, organic field effect transistors (OFET), organic thin film transistors (OTFT), organic light emitting diodes (OLED), organic light emitting transistors (OLET), organic photovoltaic devices (OPV), organic photodetectors (OPD), organic solar cells, dye sensitized solar cells (DSSC), laser diodes, Schottky diodes, photoconductors, photodetectors and thermoelectric devices.

Preferred OE devices are OFETs, OTFTs, OPVs, OPDs and OLEDs, in particular bulk heterojunction (BHJ) OPVs or inverted BHJ OPVs.

Further preferred is the use of a fullerene mixture, composition or polymer blend according to the present invention as dye in a DSSC or a perovskite-based solar cell, and a DSSC or a perovskite-based solar cell comprising a compound, composition or polymer blend according to the present invention.

The components of the above OE devices include, without limitation, charge injection layers, charge transport layers, interlayers, planarising layers, antistatic films, polymer electrolyte membranes (PEM), conducting substrates and conducting patterns.

The assemblies comprising such OE devices or components include, without limitation, integrated circuits (IC), radio frequency identification (RFID) tags or security markings or security devices containing them, flat panel displays or backlights thereof, electrophotographic devices, electrophotographic recording devices, organic memory devices, sensor devices, biosensors and biochips.

In addition the compounds and compositions of the present invention can be used as electrode materials in batteries and in components or devices for detecting and discriminating DNA sequences.

The invention further relates to a bulk heterojunction which comprises, or is being formed from, a composition comprising one or more compounds selected from formula I and one or more p-type organic semiconductor compounds that are selected from conjugated organic polymers. The invention further relates to a bulk heterojunction (BHJ) OPV device, or an inverted BHJ OPV device, comprising such a bulk heterojunction.

Terms and Definitions

As used herein, the expression that two or more compounds "differ in the nature of their adducts (or of the substituents on their adducts)" will be understood to mean that each of the compounds has at least one adduct (or substituent) which has a different structure, e.g. a different number of C atoms, than the adducts (or substituents) of the other compounds.

As used herein, any reference to "formula I" or "formula I and its subformulae" is understood to be inclusive of any specific subformula of formula I as shown hereinafter.

As used herein, the term "fullerene" will be understood to mean a compound composed of an even number of carbon atoms, which form a cage-like fused-ring having a surface which comprises six-membered rings and five-membered rings, usually with twelve five-membered rings and the rest six-membered rings, optionally with one or more atoms trapped inside. The surface of the fullerene may also contain hetero atoms like B or N.

As used herein, the term "endohedral fullerene" will be understood to mean a fullerene with one or more atoms trapped inside.

As used herein, the term "metallofullerene" will be understood to mean an endohedral fullerene wherein the atoms trapped inside are selected from metal atoms.

As used herein, the term "carbon based fullerene" will be understood to mean a fullerene without any atoms trapped inside, and wherein the surface is comprised only of carbon atoms.

As used herein, the term "polymer" will be understood to mean a molecule of high relative molecular mass, the structure of which essentially comprises the multiple repetition of units derived, actually or conceptually, from molecules of low relative molecular mass (*Pure Appl. Chem.*, 1996, 68, 2291). The term "oligomer" will be understood to mean a molecule of intermediate relative molecular mass, the structure of which essentially comprises a small plurality of units derived, actually or conceptually, from molecules of lower relative molecular mass (*Pure Appl. Chem.*, 1996, 68, 2291). In a preferred meaning as used herein present invention a polymer will be understood to mean a compound having >1, i.e. at least 2 repeat units, preferably ≥5 repeat units, and an oligomer will be understood to mean a compound with >1 and <10, preferably <5, repeat units.

Further, as used herein, the term "polymer" will be understood to mean a molecule that encompasses a backbone (also referred to as "main chain") of one or more distinct types of repeat units (the smallest constitutional unit of the molecule) and is inclusive of the commonly known terms "oligomer", "copolymer", "homopolymer" and the like. Further, it will be understood that the term polymer is inclusive of, in addition to the polymer itself, residues from initiators, catalysts and other elements attendant to the synthesis of such a polymer, where such residues are understood as not being covalently incorporated thereto. Further, such residues and other elements, while normally removed during post polymerization purification processes, are typically mixed or co-mingled with the polymer such that they generally remain with the polymer when it is transferred between vessels or between solvents or dispersion media.

As used herein, in a formula showing a polymer or a repeat unit, an asterisk (*) will be understood to mean a chemical linkage to an adjacent unit or to a terminal group in the polymer backbone. In a ring, like for example a benzene or thiophene ring, an asterisk (*) will be understood to mean a C atom that is fused to an adjacent ring.

As used herein, the terms "repeat unit", "repeating unit" and "monomeric unit" are used interchangeably and will be understood to mean the constitutional repeating unit (CRU), which is the smallest constitutional unit the repetition of which constitutes a regular macromolecule, a regular oligomer molecule, a regular block or a regular chain (*Pure Appl. Chem.*, 1996, 68, 2291). As further used herein, the term "unit" will be understood to mean a structural unit which can be a repeating unit on its own, or can together with other units form a constitutional repeating unit.

As used herein, a "terminal group" will be understood to mean a group that terminates a polymer backbone. The expression "in terminal position in the backbone" will be understood to mean a divalent unit or repeat unit that is linked at one side to such a terminal group and at the other side to another repeat unit. Such terminal groups include endcap groups, or reactive groups that are attached to a monomer forming the polymer backbone which did not participate in the polymerisation reaction, like for example a group having the meaning of $R^{23}$ or $R^{24}$ as defined below.

As used herein, the term "endcap group" will be understood to mean a group that is attached to, or replacing, a terminal group of the polymer backbone. The endcap group can be introduced into the polymer by an endcapping process. Endcapping can be carried out for example by reacting the terminal groups of the polymer backbone with a monofunctional compound ("endcapper") like for example an alkyl- or arylhalide, an alkyl- or arylstannane or an alkyl- or arylboronate. The endcapper can be added for example after the polymerisation reaction. Alternatively the endcapper can be added in situ to the reaction mixture before or during the polymerisation reaction. In situ addition of an endcapper can also be used to terminate the polymerisation reaction and thus control the molecular weight of the forming polymer. Typical endcap groups are for example H, phenyl and lower alkyl.

As used herein, the term "small molecule" will be understood to mean a monomeric compound which typically does not contain a reactive group by which it can be reacted to form a polymer, and which is designated to be used in monomeric form. In contrast thereto, the term "monomer" unless stated otherwise will be understood to mean a monomeric compound that carries one or more reactive functional groups by which it can be reacted to form a polymer.

As used herein, the terms "donor" or "donating" and "acceptor" or "accepting" will be understood to mean an electron donor or electron acceptor, respectively. "Electron donor" will be understood to mean a chemical entity that donates electrons to another compound or another group of atoms of a compound. "Electron acceptor" will be understood to mean a chemical entity that accepts electrons transferred to it from another compound or another group of atoms of a compound. See also International Union of Pure and Applied Chemistry, Compendium of Chemical Technology, Gold Book, Version 2.3.2, 19. August 2012, pages 477 and 480.

As used herein, the term "n-type" or "n-type semiconductor" will be understood to mean an extrinsic semiconductor in which the conduction electron density is in excess of the mobile hole density, and the term "p-type" or "p-type semiconductor" will be understood to mean an extrinsic semiconductor in which mobile hole density is in excess of the conduction electron density (see also, J. Thewlis, *Concise Dictionary of Physics*, Pergamon Press, Oxford, 1973).

As used herein, the term "leaving group" will be understood to mean an atom or group (which may be charged or uncharged) that becomes detached from an atom in what is considered to be the residual or main part of the molecule taking part in a specified reaction (see also *Pure Appl. Chem.*, 1994, 66, 1134).

As used herein, the term "conjugated" will be understood to mean a compound (for example a polymer) that contains mainly C atoms with $sp^2$-hybridisation (or optionally also sp-hybridisation), and wherein these C atoms may also be replaced by hetero atoms. In the simplest case this is for example a compound with alternating C—C single and double (or triple) bonds, but is also inclusive of compounds with aromatic units like for example 1,4-phenylene. The term "mainly" in this connection will be understood to mean that a compound with naturally (spontaneously) occurring defects, or with defects included by design, which may lead to interruption of the conjugation, is still regarded as a conjugated compound.

As used herein, unless stated otherwise the molecular weight is given as the number average molecular weight $M_n$ or weight average molecular weight Mw, which is determined by gel permeation chromatography (GPC) against polystyrene standards in eluent solvents such as tetrahydrofuran, trichloromethane (TCM, chloroform), chlorobenzene or 1,2,4-trichlorobenzene. Unless stated otherwise, 1,2,4-trichlorobenzene is used as solvent. The degree of polymerization, also referred to as total number of repeat units, n, will be understood to mean the number average degree of polymerization given as $n=M_n/M_U$, wherein $M_n$ is the number average molecular weight and $M_U$ is the molecular weight of the single repeat unit, see J. M. G. Cowie, *Polymers: Chemistry & Physics of Modern Materials*, Blackie, Glasgow, 1991.

As used herein, the term "carbyl group" will be understood to mean any monovalent or multivalent organic moiety which comprises at least one carbon atom either without any non-carbon atoms (like for example —C≡C—), or optionally combined with at least one non-carbon atom such as B, N, O, S, P, Si, Se, As, Te or Ge (for example carbonyl etc.).

As used herein, the term "hydrocarbyl group" will be understood to mean a carbyl group that does additionally contain one or more H atoms and optionally contains one or more hetero atoms like for example B, N, O, S, P, Si, Se, As, Te or Ge.

As used herein, the term "hetero atom" will be understood to mean an atom in an organic compound that is not a H- or C-atom, and preferably will be understood to mean B, N, O, S, P, Si, Se, As, Te or Ge.

A carbyl or hydrocarbyl group comprising a chain of 3 or more C atoms may be straight-chain, branched and/or cyclic, and may include spiro-connected and/or fused rings.

Preferred carbyl and hydrocarbyl groups include alkyl, alkoxy, thioalkyl, alkylcarbonyl, alkoxycarbonyl, alkylcarbonyloxy and alkoxycarbonyloxy, each of which is optionally substituted and has 1 to 40, preferably 1 to 25, very preferably 1 to 18 C atoms, furthermore optionally substituted aryl or aryloxy having 6 to 40, preferably 6 to 25 C atoms, furthermore alkylaryloxy, arylcarbonyl, aryloxycarbonyl, arylcarbonyloxy and aryloxycarbonyloxy, each of which is optionally substituted and has 6 to 40, preferably 7 to 40 C atoms, wherein all these groups do optionally contain one or more hetero atoms, preferably selected from B, N, O, S, P, Si, Se, As, Te and Ge.

Further preferred carbyl and hydrocarbyl group include for example: a $C_1$-$C_{40}$ alkyl group, a $C_1$-$C_{40}$ fluoroalkyl group, a $C_1$-$C_{40}$ alkoxy or oxaalkyl group, a $C_2$-$C_{40}$ alkenyl group, a $C_2$-$C_{40}$ alkynyl group, a $C_3$-$C_{40}$ allyl group, a $C_4$-$C_{40}$ alkyldienyl group, a $C_4$-$C_{40}$ polyenyl group, a $C_2$-$C_{40}$ ketone group, a $C_2$-$C_{40}$ ester group, a $C_6$-$C_{18}$ aryl group, a $C_6$-$C_{40}$ alkylaryl group, a $C_6$-$C_{40}$ arylalkyl group, a $C_4$-$C_{40}$ cycloalkyl group, a $C_4$-$C_{40}$ cycloalkenyl group, and the like. Preferred among the foregoing groups are a $C_1$-$C_{20}$ alkyl group, a $C_1$-$C_{20}$ fluoroalkyl group, a $C_2$-$C_{20}$ alkenyl group, a $C_2$-$C_{20}$ alkynyl group, a $C_3$-$C_{20}$ allyl group, a $C_4$-$C_{20}$ alkyldienyl group, a $C_2$-$C_{20}$ ketone group, a $C_2$-$C_{20}$ ester group, a $C_6$-$C_{12}$ aryl group, and a $C_4$-$C_{20}$ polyenyl group, respectively.

Also included are combinations of groups having carbon atoms and groups having hetero atoms, like e.g. an alkynyl group, preferably ethynyl, that is substituted with a silyl group, preferably a trialkylsilyl group.

The carbyl or hydrocarbyl group may be an acyclic group or a cyclic group. Where the carbyl or hydrocarbyl group is an acyclic group, it may be straight-chain or branched. Where the carbyl or hydrocarbyl group is a cyclic group, it may be a non-aromatic carbocyclic or heterocyclic group, or an aryl or heteroaryl group.

A non-aromatic carbocyclic group as referred to above and below is saturated or unsaturated and preferably has 4 to 30 ring C atoms. A non-aromatic heterocyclic group as referred to above and below preferably has 4 to 30 ring C atoms, wherein one or more of the C ring atoms are optionally replaced by a hetero atom, preferably selected from N, O, S, Si and Se, or by a —S(O)— or —S(O)$_2$— group. The non-aromatic carbo- and heterocyclic groups are mono- or polycyclic, may also contain fused rings, preferably contain 1, 2, 3 or 4 fused or unfused rings, and are optionally substituted with one or more groups L, wherein L is selected from halogen, —CN, —NC, —NCO, —NCS, —OCN, —SCN, —C(=O)NR$^0$R$^{00}$, —C(=O)X$^0$, —C(=O)R$^0$, —NH$_2$, —NR$^0$R$^{00}$, —SH, —SR$^0$, —SO$_3$H, —SO$_2$R$^0$, —OH, —NO$_2$, —CF$_3$, —SF$_5$, optionally substituted silyl, or carbyl or hydrocarbyl with 1 to 40 C atoms that is optionally substituted and optionally comprises one or more hetero atoms, and is preferably alkyl, alkoxy, thioalkyl, alkylcarbonyl, alkoxycarbonyl, alkylcarbonyloxy or alkoxycarbonyloxy with 1 to 20 C atoms that is optionally fluorinated, $X^0$ is halogen, preferably F, Cl or Br, and $R^0$, $R^{00}$ have the meanings given above and below, and preferably denote H or alkyl with 1 to 12 C atoms.

Preferred substituents L are selected from halogen, most preferably F, or alkyl, alkoxy, oxaalkyl, thioalkyl, fluoroalkyl and fluoroalkoxy with 1 to 12 C atoms, or alkenyl or alkynyl with 2 to 12 C atoms.

Preferred non-aromatic carbocyclic or heterocyclic groups are tetrahydrofuran, indane, pyran, pyrrolidine, piperidine, cyclopentane, cyclohexane, cycloheptane, cyclopentanone, cyclohexanone, dihydro-furan-2-one, tetrahydro-pyran-2-one and oxepan-2-one.

An aryl group as referred to above and below preferably has 4 to 30 ring C atoms, is mono- or polycyclic and may also contain fused rings, preferably contains 1, 2, 3 or 4 fused or unfused rings, and is optionally substituted with one or more groups L as defined above.

A heteroaryl group as referred to above and below preferably has 4 to 30 ring C atoms, wherein one or more of the C ring atoms are replaced by a hetero atom, preferably selected from N, O, S, Si and Se, is mono- or polycyclic and may also contain fused rings, preferably contains 1, 2, 3 or 4 fused or unfused rings, and is optionally substituted with one or more groups L as defined above.

As used herein, "arylene" will be understood to mean a divalent aryl group, and "heteroarylene" will be understood to mean a divalent heteroaryl group, including all preferred meanings of aryl and heteroaryl as given above and below.

Preferred aryl and heteroaryl groups are phenyl in which, in addition, one or more CH groups may be replaced by N, naphthalene, thiophene, selenophene, thienothiophene, dithienothiophene, fluorene and oxazole, all of which can be unsubstituted, mono- or polysubstituted with L as defined above. Very preferred rings are selected from pyrrole, preferably N-pyrrole, furan, pyridine, preferably 2- or 3-pyridine, pyrimidine, pyridazine, pyrazine, triazole, tetrazole, pyrazole, imidazole, isothiazole, thiazole, thiadiazole, isoxazole, oxazole, oxadiazole, thiophene, preferably 2-thiophene, selenophene, preferably 2-selenophene, thieno[3,2-b]thiophene, thieno[2,3-b]thiophene, furo[3,2-b]furan, furo[2,3-b]furan, seleno[3,2-b]selenophene, seleno[2,3-b]selenophene, thieno[3,2-b]selenophene, thieno[3,2-b]furan, indole, isoindole, benzo[b]furan, benzo[b]thiophene, benzo[1,2-b;4,5-b']dithiophene, benzo[2,1-b;3,4-b']dithiophene, quinole, 2-methylquinole, isoquinole, quinoxaline, quinazoline, benzotriazole, benzimidazole, benzothiazole, benzisothiazole, benzisoxazole, benzoxadiazole, benzoxazole, benzothiadiazole, 4H-cyclopenta[2,1-b;3,4-b']dithiophene, 7H-3,4-dithia-7-sila-cyclopenta[a]pentalene, all of which can be unsubstituted, mono- or polysubstituted with L as defined above. Further examples of aryl and heteroaryl groups are those selected from the groups shown hereinafter.

An alkyl group or an alkoxy group, i.e., where the terminal $CH_2$ group is replaced by —O—, can be straight-chain or branched. It is preferably straight-chain, has 2, 3, 4, 5, 6, 7, 8, 12 or 16 carbon atoms and accordingly is preferably ethyl, propyl, butyl, pentyl, hexyl, heptyl, octyl, dodecyl or hexadecyl, ethoxy, propoxy, butoxy, pentoxy, hexoxy, heptoxy, octoxy, dodecoxy or hexadecoxy, furthermore methyl, nonyl, decyl, undecyl, tridecyl, tetradecyl, pentadecyl, nonoxy, decoxy, undecoxy, tridecoxy or tetradecoxy, for example.

An alkenyl group, i.e., wherein one or more $CH_2$ groups are replaced by —CH=CH— can be straight-chain or branched. It is preferably straight-chain, has 2 to 10 C atoms and accordingly is preferably vinyl, prop-1-, or prop-2-enyl, but-1-, 2- or but-3-enyl, pent-1-, 2-, 3- or pent-4-enyl, hex-1-, 2-, 3-, 4- or hex-5-enyl, hept-1-, 2-, 3-, 4-, 5- or hept-6-enyl, oct-1-, 2-, 3-, 4-, 5-, 6- or oct-7-enyl, non-1-, 2-, 3-, 4-, 5-, 6-, 7- or non-8-enyl, dec-1-, 2-, 3-, 4-, 5-, 6-, 7-, 8- or dec-9-enyl.

Especially preferred alkenyl groups are $C_2$-$C_7$-1E-alkenyl, $C_4$-$C_7$-3E-alkenyl, $C_5$-$C_7$-4-alkenyl, $C_6$-$C_7$-5-alkenyl and $C_7$-6-alkenyl, in particular $C_2$-$C_7$-1E-alkenyl, $C_4$-$C_7$-3E-alkenyl and $C_5$-$C_7$-4-alkenyl. Examples for particularly preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 C atoms are generally preferred.

An oxaalkyl group, i.e., where one $CH_2$ group is replaced by —O—, is preferably straight-chain 2-oxapropyl (=methoxymethyl), 2-(=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8- or 9-oxadecyl, for example.

In an alkyl group wherein one $CH_2$ group is replaced by —O— and one $CH_2$ group is replaced by —C(O)—, these radicals are preferably neighboured. Accordingly these radicals together form a carbonyloxy group —C(O)—O— or an oxycarbonyl group —O—C(O)—. Preferably this group is straight-chain and has 2 to 6 C atoms. It is accordingly preferably acetyloxy, propionyloxy, butyryloxy, pentanoyloxy, hexanoyloxy, acetyloxymethyl, propionyloxymethyl, butyryloxymethyl, pentanoyloxymethyl, 2-acetyloxyethyl, 2-propionyloxyethyl, 2-butyryloxyethyl, 3-acetyloxypropyl, 3-propionyloxypropyl, 4-acetyloxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl, 4-(methoxycarbonyl)-butyl.

An alkyl group wherein two or more $CH_2$ groups are replaced by —O— and/or —C(O)O— can be straight-chain or branched. It is preferably straight-chain and has 3 to 12 C atoms. Accordingly it is preferably bis-carboxy-methyl, 2,2-bis-carboxy-ethyl, 3,3-bis-carboxy-propyl, 4,4-bis-carboxy-butyl, 5,5-bis-carboxy-pentyl, 6,6-bis-carboxy-hexyl, 7,7-bis-carboxy-heptyl, 8,8-bis-carboxy-octyl, 9,9-bis-carboxy-nonyl, 10,10-bis-carboxy-decyl, bis-(methoxycarbonyl)-methyl, 2,2-bis-(methoxycarbonyl)-ethyl, 3,3-bis-(methoxycarbonyl)-propyl, 4,4-bis-(methoxycarbonyl)-butyl, 5,5-bis-(methoxycarbonyl)-pentyl, 6,6-bis-(methoxycarbonyl)-hexyl, 7,7-bis-(methoxycarbonyl)-heptyl, 8,8-bis-(methoxycarbonyl)-octyl, bis-(ethoxycarbonyl)-methyl, 2,2-bis-(ethoxycarbonyl)-ethyl, 3,3-bis-(ethoxycarbonyl)-propyl, 4,4-bis-(ethoxycarbonyl)-butyl, 5,5-bis-(ethoxycarbonyl)-hexyl.

A thioalkyl group, i.e., where one $CH_2$ group is replaced by —S—, is preferably straight-chain thiomethyl (—$SCH_3$), 1-thioethyl (—$SCH_2CH_3$), 1-thiopropyl (=—$SCH_2CH_2CH_3$), 1-(thiobutyl), 1-(thiopentyl), 1-(thiohexyl), 1-(thioheptyl), 1-(thiooctyl), 1-(thiononyl), 1-(thiodecyl), 1-(thioundecyl) or 1-(thiododecyl), wherein preferably the $CH_2$ group adjacent to the $sp^2$ hybridised vinyl carbon atom is replaced.

A fluoroalkyl group is perfluoroalkyl $C_iF_{2i+1}$, wherein i is an integer from 1 to 15, in particular $CF_3$, $C_2F_5$, $C_3F_7$, $C_4F_9$, $C_5F_{11}$, $C_6F_{13}$, $C_7F_{15}$ or $C_8F_{17}$, very preferably $C_6F_{13}$, or partially fluorinated alkyl, preferably with 1 to 15 C atoms, in particular 1,1-difluoroalkyl, all of the aforementioned being straight-chain or branched.

Preferably "fluoroalkyl" means a partially fluorinated (i.e. not perfluorinated) alkyl group.

Alkyl, alkoxy, alkenyl, oxaalkyl, thioalkyl, carbonyl and carbonyloxy groups can be achiral or chiral groups. Particularly preferred chiral groups are 2-butyl (=1-methylpropyl), 2-methylbutyl, 2-methylpentyl, 3-methylpentyl, 2-ethylhexyl, 2-butyloctyl, 2-hexyldecyl, 2-octyldodecyl, 2-propylpentyl, in particular 2-methylbutyl, 2-methylbutoxy, 2-methylpentoxy, 3-methylpentoxy, 2-ethyl-hexoxy, 2-butyloctoxyo, 2-hexyldecoxy, 2-octyldodecoxy, 1-methylhexoxy, 2-octyloxy, 2-oxa-3-methylbutyl, 3-oxa-4-methylpentyl, 4-methylhexyl, 2-hexyl, 2-octyl, 2-nonyl, 2-decyl, 2-dodecyl, 6-methoxy-octoxy, 6-methyloctoxy, 6-methyloctanoyloxy, 5-methylheptyloxy-carbonyl, 2-methylbutyryloxy, 3-methylvaleroyloxy, 4-methylhexanoyloxy, 2-chloropropionyloxy, 2-chloro-3-methylbutyryloxy, 2-chloro-4-methyl-valeryl-oxy, 2-chloro-3-methylvaleryloxy, 2-methyl-3-oxapentyl, 2-methyl-3-oxa-hexyl, 1-methoxy-propyl-2-oxy, 1-ethoxypropyl-2-oxy, 1-propoxypropyl-2-oxy, 1-butoxypropyl-2-oxy, 2-fluorooctyloxy, 2-fluorodecyloxy, 1,1,1-trifluoro-2-octyloxy, 1,1,1-trifluoro-2-octyl, 2-fluoromethyloctyloxy for example. Very preferred are 2-ethylhexyl, 2-butyloctyl, 2-hexyldecyl, 2-octyldodecyl, 2-hexyl, 2-octyl, 2-octyloxy, 1,1,1-trifluoro-2-hexyl, 1,1,1-trifluoro-2-octyl and 1,1,1-trifluoro-2-octyloxy.

Preferred achiral branched groups are isopropyl, isobutyl (=methylpropyl), isopentyl (=3-methylbutyl), tert. butyl, isopropoxy, 2-methyl-propoxy and 3-methylbutoxy.

In a preferred embodiment, the alkyl groups are independently of each other selected from primary, secondary or tertiary alkyl or alkoxy with 1 to 30 C atoms, wherein one or more H atoms are optionally replaced by F, or aryl, aryloxy, heteroaryl or heteroaryloxy that is optionally alkylated or alkoxylated and has 4 to 30 ring atoms. Very preferred groups of this type are selected from the group consisting of the following formulae

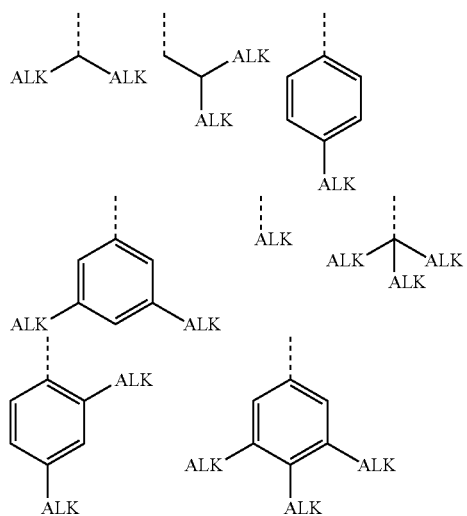

wherein "ALK" denotes optionally fluorinated, preferably linear, alkyl or alkoxy with 1 to 20, preferably 1 to 12 C-atoms, in case of tertiary groups very preferably 1 to 9 C atoms, and the dashed line denotes the link to the ring to which these groups are attached. Especially preferred among these groups are those wherein all ALK subgroups are identical.

As used herein, "halogen" or "hal" means F, Cl, Br or I, preferably F, Cl or Br.

As used herein, —CO—, —C(=O)— and —C(O)— will be understood to mean a carbonyl group, i.e. a group having the structure

As used herein, C=CR$^1$R$^2$ will be understood to mean an ylidene group, i.e. a group having the structure

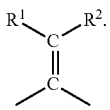

Above and below, Y$^1$ and Y$^2$ are independently of each other H, F, Cl or CN.

Above and below, R$^0$ and R$^{00}$ are independently of each other H or an optionally substituted carbyl or hydrocarbyl group with 1 to 40 C atoms, and preferably denote H or alkyl with 1 to 12 C-atoms.

DETAILED DESCRIPTION

The fullerene mixture comprising two or more compounds of formula I demonstrates one or more of the following improved properties compared to previously disclosed fullerene derivatives and mixtures for OPV/OPD application:

i) The substitution in positions (R)$_p$, which can each possess any number of solubilising groups, enable greater light stability of the bulk heterojunction through mediation of the fullerene 2+2 Diels Alder dimerisation/oligomerisation reaction, as described, for example in *Adv. Energy Mater.* 2014, 4, 1300693 and ACS Nano 2014, 8 (2), 1297-1308.

ii) The substitution in positions (R)$_p$, which can each possess any number of solubilising groups, enable greater stability towards light illumination of the bulk heterojunction through mediation of the fullerene crystallisation and/or phase separation kinetic, thus stabilising the initial equilibrium thermodynamics in the BHJ.

iii) The substitution in positions (R)$_p$, which can each possess any number of solubilising groups, enable greater thermal stability of the bulk heterojunction through mediation of the fullerene crystallisation and/or phase separation kinetic, thus stabilising the initial equilibrium thermodynamics in the BHJ.

iv) The electron accepting and/or donating unit(s) in positions (R)$_p$, Ar$^1$ and Ar$^2$ reduce the fullerene band-gap and therefore the potential for improved light absorption.

v) Additional fine-tuning of the electronic energies (HOMO/LUMO levels) results by careful selection of the electron accepting and/or donating unit(s) in positions (R)n to increase the open circuit potential (V$_{oc}$).

vi) Additional fine-tuning of the electronic energies (HOMO/LUMO levels) result by careful selection of the electron accepting and/or donating unit(s) in position positions (R)$_p$, Ar$^1$ and/or Ar$^2$ to reduce the energy loss in the electron transfer process between the fullerene and the p-type material (i.e. polymer, oligomer, a define molecular unit) in the active layer.

vii) The substitution in positions $(R)_p$, which can each possess more than one solubilising group, may enable higher fullerene solubility in non-halogenated solvents due to the increased number of solubilising groups.

The fullerene $C_n$ in formula I and its subformulae may be composed of any number n of carbon atoms Preferably, in the compounds of formula I and its subformulae the number of carbon atoms n of which the fullerene $C_n$ is composed is 60, 70, 76, 78, 82, 84, 90, 94 or 96, very preferably 60 or 70.

In addition to the provisos a)-c) above, the mixture according to the present invention may also comprise two or more compounds of formula I which are differing in their number n of carbon atoms forming the fullerene.

Thus, in a further preferred embodiment of the present invention the fullerene mixture comprises a C60 fullerene and a higher fullerene, which is preferably selected from C70, C76, C78, C82, C84, C90, C94 or C96, and is very preferably C70, wherein the C60 fullerene and the higher fullerene differ in at least one of
the nature of their adducts $Ad^1$,
the nature of substituents R on their adducts $Ad^1$,
the number p of substituents R on their adducts $Ad^1$.

The fullerene $C_n$ in formula I and its subformulae is preferably selected from carbon based fullerenes, endohedral fullerenes, or mixtures thereof, very preferably from carbon based fullerenes.

Suitable and preferred carbon based fullerenes include, without limitation, $(C_{60-Ih})[5,6]$fullerene, $(C_{70-D5h})[5,6]$fullerene, $(C_{76-D2*})[5,6]$fullerene, $(C_{84-D2*})[5,6]$fullerene, $(C_{84-D2d})[5,6]$fullerene, or a mixture of two or more of the aforementioned carbon based fullerenes.

The endohedral fullerenes are preferably metallofullerenes. Suitable and preferred metallofullerenes include, without limitation, La@$C_{60}$, La@$C_{82}$, Y@$C_{82}$, $Sc_3N@C_{80}$, $Y_3N@C_{80}$, $Sc_3C_2@C_{80}$ or a mixture of two or more of the aforementioned metallofullerenes.

The adduct $Ad^1$ is preferably appended to the fullerene $C_n$ by a [6,6]-bond and/or [5,6]-bond, preferably by a [6,6]-bond.

In case $C_n$ is a less symmetric fullerene, like for example C70, the compound of formula I may also comprise a mixture of regioisomers in which the adduct $Ad^1$ is appended to different bonds of the fullerene, as disclosed for example in C. Thilgen and F. Diederich, Top. Curr. Chem. 1999, 199, 135-171.

The fullerene compounds of formula I may also undergo fullerene 2+2 Diels Alder dimerisation/oligomerisation reaction, as described, for example in Adv. Energy Mater. 2014, 4, 1300693 and ACS Nano 2014, 8 (2), 1297-1308.

In the compounds of formula I and its subformulae, o preferably denotes 1, 2, 3 or 4, very preferably 1 or 2. In another preferred embodiment, o is a non-integer >1 like 1.5.

In the compounds of formula I and its subformulae, p preferably denotes 0, 1, 2, 3 or 4, very preferably 1 or 2.

Especially preferred are adducts $Ad^1$ selected from formula 1 and 2, very preferably from formula 1.

Preferred adducts $Ad^1$ are selected from the following formulae

1-1

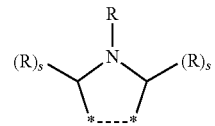
2-1

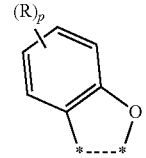
3-1

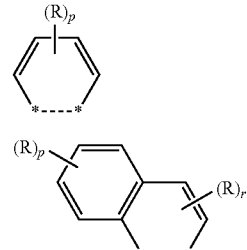
4-1

5-1

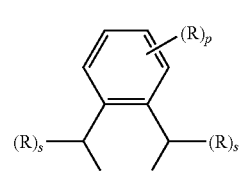
6-1

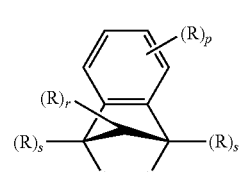
7-1

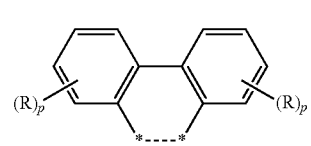
8-1

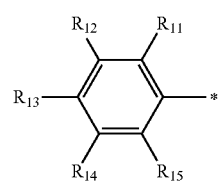

wherein R and p have the meanings of formula I or one of the preferred meanings as given above and below, p is preferably 0, 1, 2, 3 or 4, r is 0, 1 or 2 and s is 0 or 1.

In formulae 3-1, 4-1 and 8-1 preferably at least one index p is different from 0 and is preferably 1 or 2. In formula 2-1 preferably at least one index s is 1. In formula 5-1 preferably at least one of p and r is different from 0 and is preferably 1 or 2. In formulae 6-1 and 7-1 preferably at least one of p and s is different from 0, and preferably s is 1 and/or p is 1 or 2.

In the compounds of formula I and its subformulae the substituents R on the adduct $Ad^1$ are preferably selected from the following groups:

C-1

$R_{12}$ $R_{11}$ $R_{13}$ — *

$R_{14}$ $R_{15}$

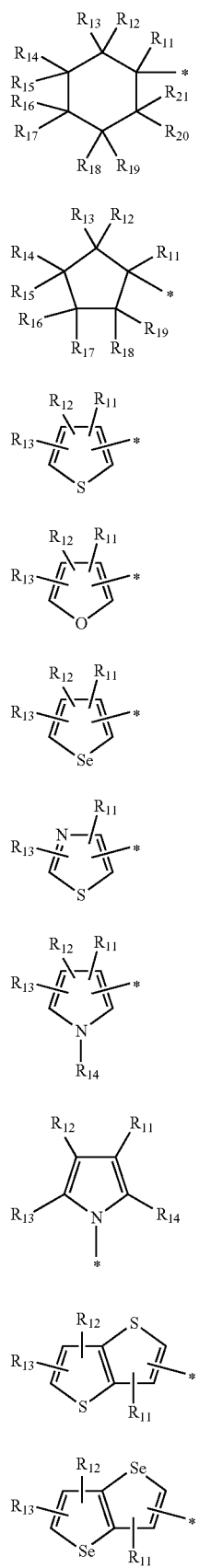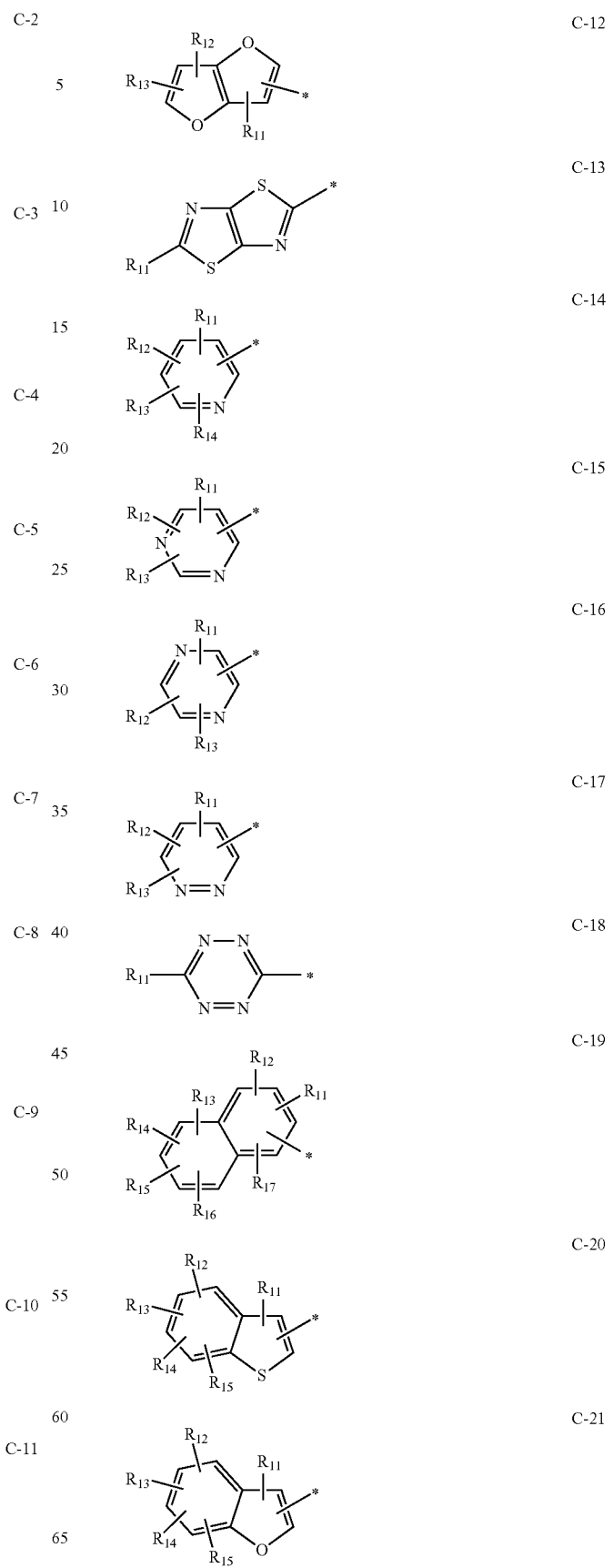

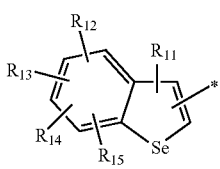
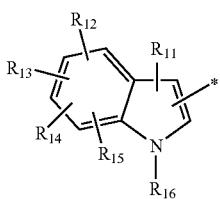
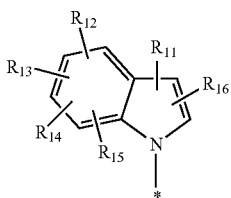
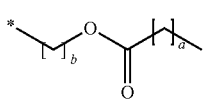

C-25

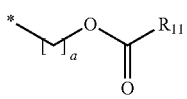

C-26

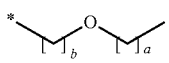

C-27

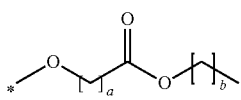

C-28

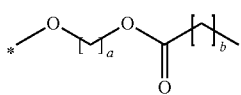

C-29

C-30

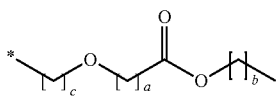

C-31

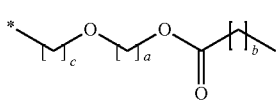

C-32

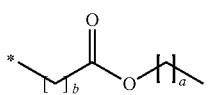

C-33

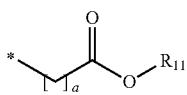

C-34

C-22

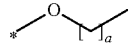

C-35 wherein the individual radicals, independently of each other, and on each occurrence identically or differently, have the following meanings a 0 or an integer from 1 to 9, preferably 0 or an integer from 1 to 6, b 0 or an integer from 1 to 9, preferably 0 or an integer from 1 to 6, c 0 or an integer from 1 to 9, preferably 0 or an integer from 1 to 6, $R^{11}$ to $R^{19}$ denote H, halogen, CN, an alkyl group with 1 to 50 C atoms, which is straight-chain, branched or cyclic, and in which one or more $CH_2$ groups are optionally replaced by —O—, —S—, —C(=O)—, —C(=S)—, —C(=O)—O—, —O—C(=O)—, —NR$^o$—, —C(=O)—NR$^o$—, —NR$^o$—C(=O)—, —SiR$^o$R$^{oo}$—, —CF$_2$—, —CR$^o$=CR$^o$—, —CR$^o$=N—, —N=N—, or —C≡C— in such a manner that O and/or S atoms are not linked directly to one another, and/or in which one or more H atoms are optionally replaced by F, Cl, Br, I or CN, or denote a saturated or unsaturated, non-aromatic carbo- or heterocyclic group, or an aryl, aryloxy, aryloxycarbonyl, arylcarbonyloxy, heteroaryl, heteroaryloxy, heteroaryloxycarbonyl or heteroarylcarbonyloxy group, wherein each of the aforementioned cyclic groups has 5 to 20 ring atoms, is mono- or polycyclic, does optionally contain fused rings, and is optionally substituted by one or more identical or different groups L as defined in formula I, $R^o$, $R^{oo}$ are as defined in formula I.

Preferred substituents $R^{11-19}$ are independently of each other selected from alkyl, alkoxy, thioalkyl, alkoxycarbonyl and alkylcarbonyloxy with 1 to 30, preferably 4 to 20 C atoms, in which one or more $CH_2$ groups are optionally replaced by —O—, —S—, —C(O)—, —C(S)—, —C(O)—O—, —O—C(O)—, —NR$^o$—, —SiR$^o$R$^{oo}$—, —CF$_2$—, furthermore aryl, aryloxy, aryloxycarbonyl, arylcarbonyloxy, heteroaryl, heteroaryloxy, heteroaryloxycarbonyl and heteroarylcarbonyloxy with 5 to 15 ring atoms which are optionally substituted by one or more groups L as defined above and below.

Above and below, $R^o$ and $R^{oo}$ preferably denote, independently of each other, H or alkyl with 1 to 12 C-atoms.

In the adducts of formulae 3 and 5 to 8, $Ar^1$ and $Ar^2$ preferably denote, independently of each other, an aryl or heteroaryl group with 5 to 20, preferably 5 to 15, ring atoms, which is mono- or polycyclic, and which is preferably substituted by one or more, preferably two or more, identical or different substituents R, $R^{11}$ or L that are preferably selected from halogen, very preferably F, straight-chain, branched or cyclic alkyl with 1 to 30, preferably 4 to 20, very preferably 5 to 15, C atoms, in which one or more $CH_2$ groups are optionally replaced by —O—, —S—, —C(O)—, —C(S)—, —C(O)—O—, —O—C(O)—, —S(O)$_2$—, —NR$^o$—, —SiR$^o$R$^{oo}$—, —CF$_2$—, wherein $R^o$ and $R^{oo}$ have one of the meanings given above and below.

Very preferably $Ar^1$ and $Ar^2$ are selected from the following groups:

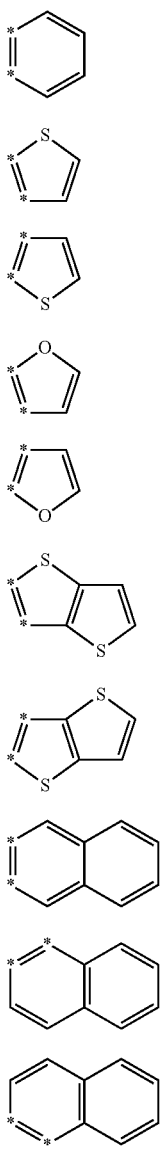

(P-F-C-1)

(P-F-C-2)

(P-F-C-3)

(P-F-C-4)

(P-F-C-5)

(P-F-C-6)

(P-F-C-7)

(P-F-C-8)

(P-F-C-9)

(P-F-C-10)

which are optionally substituted by one or more groups $R^{11}$ or L as defined above and below.

Most preferably $Ar^1$ and $Ar^2$ denote benzene, thiophene or naphthalene that is optionally substituted by one or more groups R, $R^{11}$ or L as defined above.

In addition to the first adduct $Ad^1$ in formula I, the fullerene $C_n$ may have any number (m) of second adducts $Ad^2$ different from $Ad^1$. The second adduct $Ad^2$ may be any possible adduct or combination of adducts with any connectivity to the fullerene.

The adduct $Ad^2$ is preferably appended to the fullerene $C_n$ by the [6,6]-bond and/or [5,6]-bond, preferably on at least one [6,6]-bond.

In the compounds of formula I and its subformulae, the number m of second adducts $Ad^2$ appended to the fullerene $C_n$ is 0, an integer ≥1, or a non-integer >0 like 0.5 or 1.5, and is preferably 0, 1 or 2.

In a preferred embodiment the number m of the second adducts $Ad^2$ appended to the fullerene $C_n$ is 0.

In another preferred embodiment the number m of the second adducts $Ad^2$ appended to the fullerene $C_n$ is >0, preferably 1 or 2.

The second adduct $Ad^2$ in formula I and its subformulae is preferably selected from the following formulae

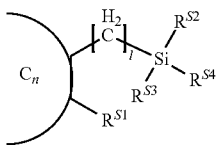

S-1

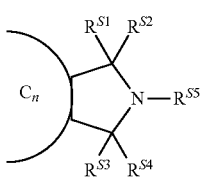

S-2

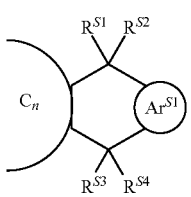

S-3

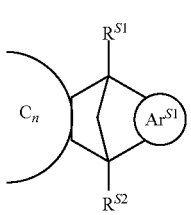

S-4

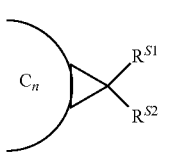

S-5

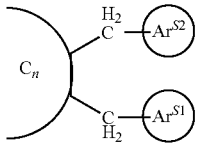

S-6

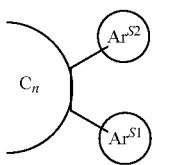

S-7

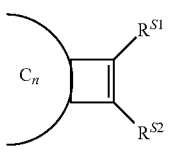

S-8

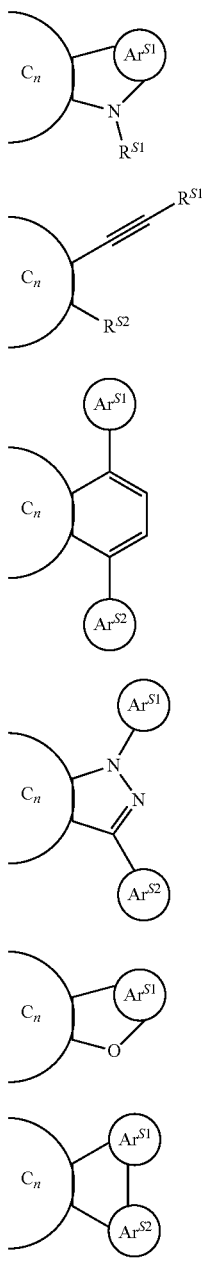

wherein $R^{S1}$, $R^{S2}$, $R^{S3}$, $R^{S4}$ and $R^{S5}$ independently of each other denote H, halogen or CN, or have one of the meanings of $R^{11}$ or L as given above and below, and $Ar^{S1}$ and $Ar^{S2}$ have independently of each other one of the meanings of $Ar^1$ in formula 4 or one of its preferred meanings as given above and below.

In the compounds of formula I and its subformulae, all adducts $Ad^1$ and $Ad^2$ may be connected to one another in any combination in the finished product or during synthesis, to facilitate preferred properties in the finished product.

Preferred fullerenes of formula I are selected from methanofullerene derivatives, Prato fullerene derivatives, Bingel fullerene derivatives, diazoline fullerene derivatives, and Diels-Alder fullerene derivatives, all of which are known from and disclosed in prior art, for example in US 2013/0306944 A1 and the literature cited therein. A preferred mixture according to the present invention comprises two or more fullerenes selected form the aforementioned fullerene derivatives, which differ in at least one of the nature of their adducts,
the nature of substituents to their adducts,
the number of substituents to their adducts.

Very preferred compounds of formula I and its subformulae are selected from the following preferred embodiments, including any combination thereof:

m is 0,
o is 1 or 2,
m is 0 and o is 1 or 2,
p is 0, 1, 2, 3 or 4,
n is 60 or 70,
n is 60,
$Ad^1$ is selected of formula 1,
$Ar^1$ and $Ar^2$ denote benzene, thiophene or naphthalene that is optionally substituted by one or more groups $R^{11}$ or L,
R is selected from benzene, thiophene or naphthalene that is optionally fluorinated, alkylated or alkoxylated, or from alkyl, fluorinated alkyl, alkoxy, thioalkyl, —COO-alkyl, alkyl-COO-alkyl, —CO-alkyl, with "alkyl" in each occurrence having from 1 to 20, preferably from 1 to 12 C atoms.

Preferred compounds of formula I are selected from the following subformulae

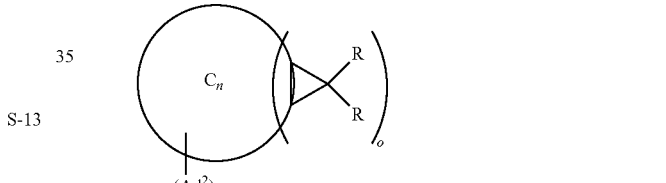

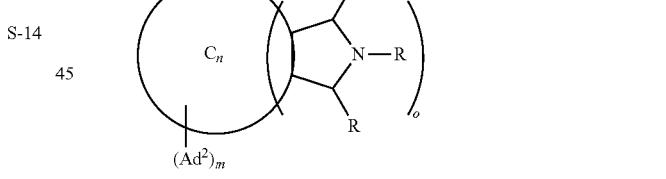

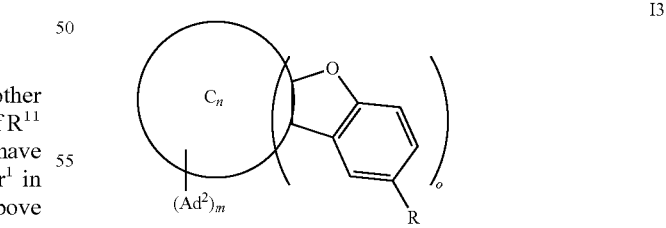

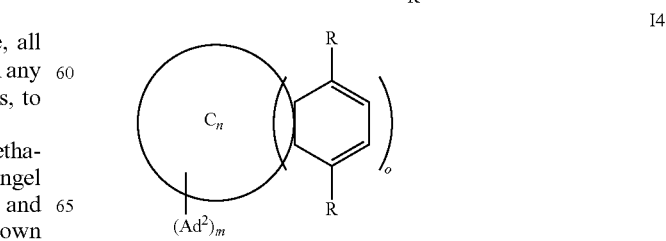

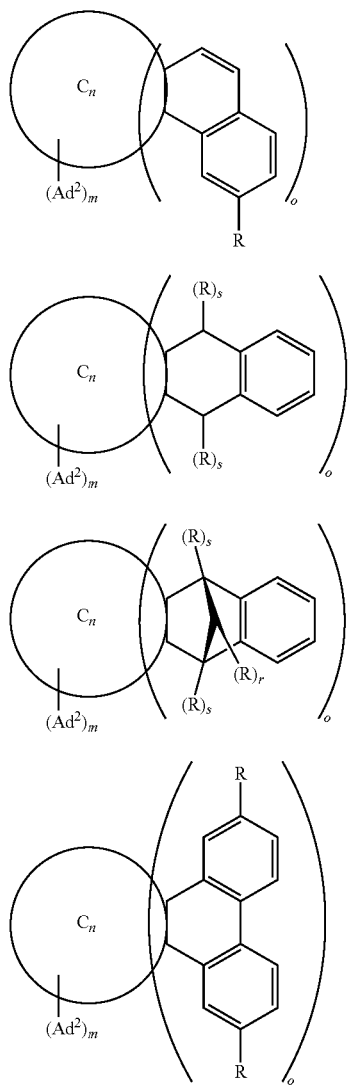

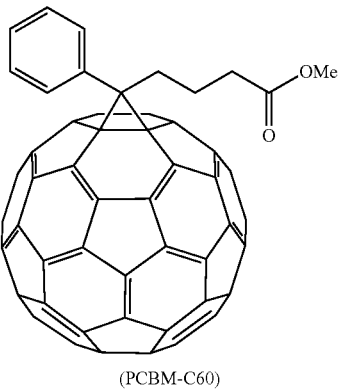
(PCBM-C60)

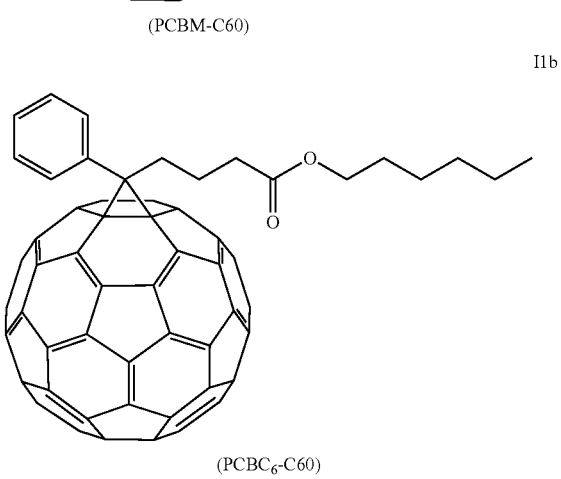
(PCBC$_6$-C60)

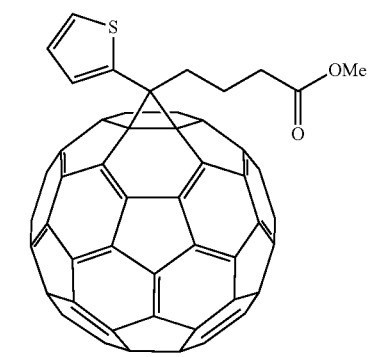

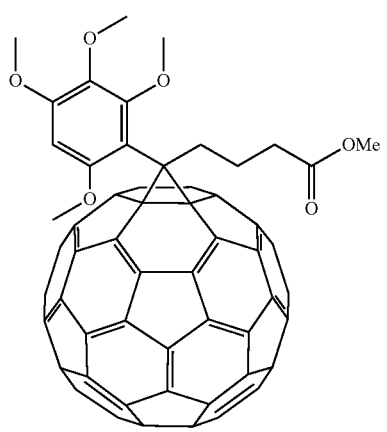

wherein $C_n$, m, $Ad^2$, R, o and s have the meanings given in formula I and formulae 1-1 to 8-1, or one of the preferred meanings as given above and below, m is preferably 0, o is preferably 1 or 2, very preferably 1, and in formulae I3-I8 the benzene rings of the adduct are optionally substituted by one or more further groups R.

Very preferred are compounds of formula I1-I8 wherein $C_n$ is C60 or C70.

Very preferred are compounds of formula I1.

Further preferred are compounds of formula I1 wherein m is 0, o is 1 or 2, one substituent R is benzene, thiophene or naphthalene which are optionally substituted by one or more groups $R^{11}$, and the other substituent R is an ester group, preferably selected from formulae C-33 and C-34.

Further preferred are compounds of formula I1 wherein m is 0, o is 1 or 2, one substituent R is benzene, thiophene or naphthalene, and the other substituent R is an ester group of formula C-34, wherein a is 1, 2, 3, 4, 5, or 6, very preferably 3, and $R^{11}$ is alkyl with 1 to 15 C-atoms, preferably methyl, ethyl, propyl, butyl, pentyl or hexyl.

Examples of preferred compounds of formulae I1-I8 are listed below

I1e

I1f

I1g
(PCBC₃-C60)

I1h

I1i

I2a

I2b

I2c

-continued
I2d
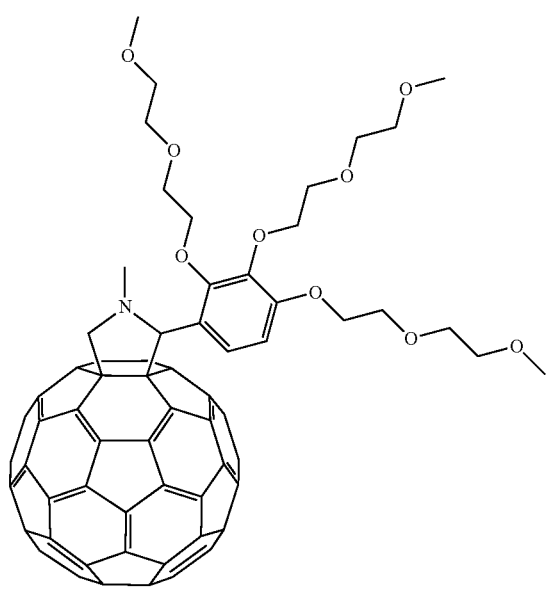
I2e
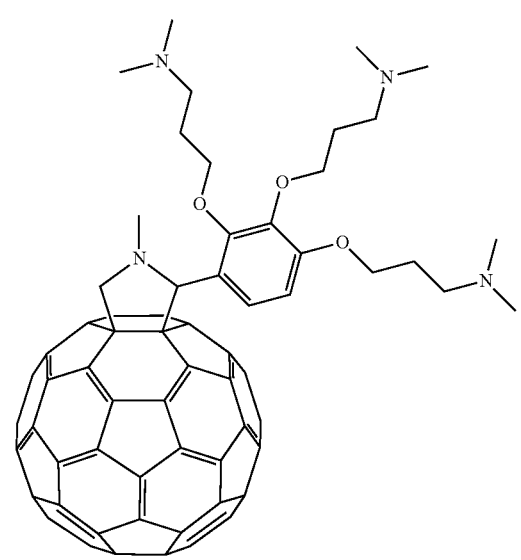
I3a
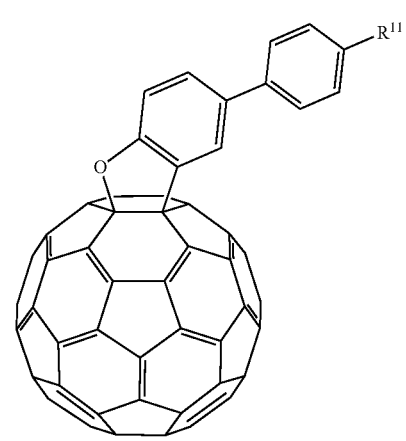
-continued
I4a
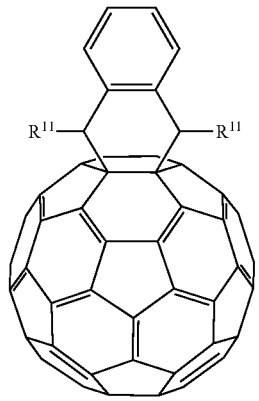
I6a
I6b
I6c
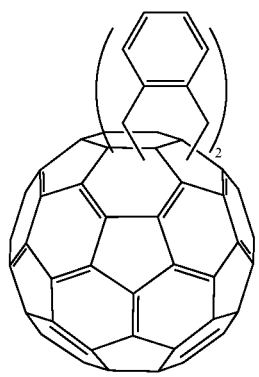

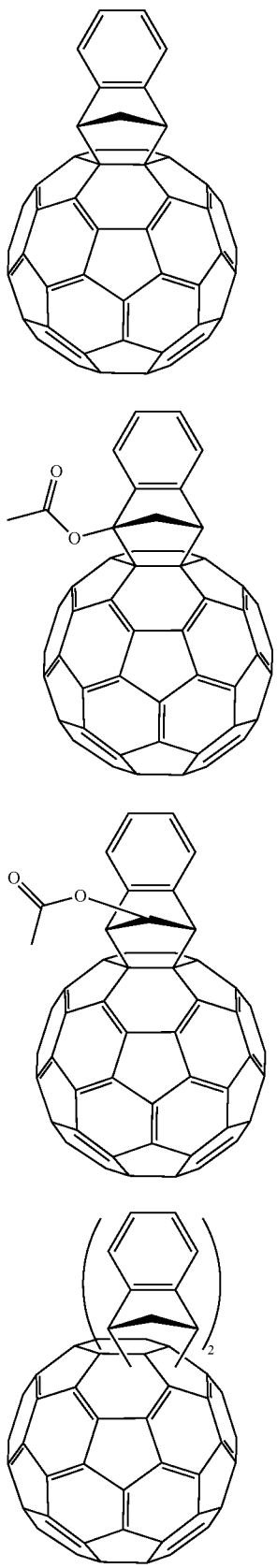

I7a
I7b
I7c
I7d

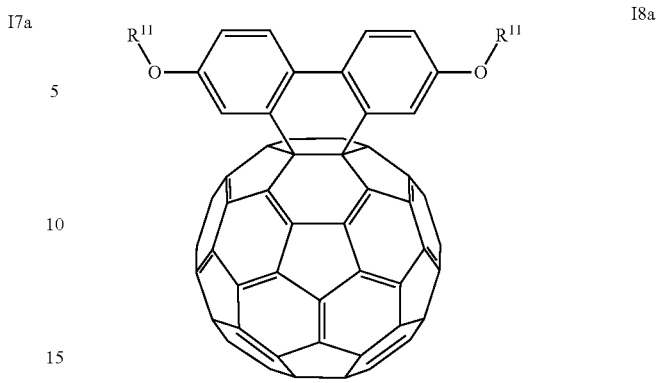

I8a wherein $R^{11}$ has one of the meanings given above and below, and preferably denotes alkyl with 1 to 12 C atoms, Me is a methyl group, and the fullerene is C60.

Further preferred compounds are those of formula I1a-I8a shown above, but wherein the C60 fullerene is replaced by a C70 fullerene.

Very preferred are mixtures comprising two or more compounds of formula I, preferably selected from formulae I1-I8, which are differing in the nature of their substituents R.

Further preferred are mixtures comprising
a compound of formula I1 a and a compound selected from formulae I1 b, I1c, I1d, I1e, I1f, I1g, I1h and I1i, or
a compound of formula I1a and a compound selected from formulae I2a, I2b, I2c, I2d and I2e or
a compound of formula I1a and a compound of formula I3a, or
a compound of formula I1a and a compound of formula I4a, or
a compound of formula I1a and a compound selected from formulae I6a, I6b and I6c, or
a compound of formula I1a and a compound selected from formulae I7a, I7b, I7c and I7d, or
a compound of formula I1a and a compound of formula I8a, or
a compound selected from formulae I6a, I6b and I6c and a compound selected from formulae I7a, I7b, I7c and I7d.

Further preferred are mixtures comprising
a first compound of formula I1, wherein m is 0, o is 1 or 2, and wherein one substituent R is benzene, and the other substituent R is an ester group of formula C-34, wherein a is 3, and $R^{11}$ is methyl (PCBM),
a second compound of formula I1, wherein m is 0, o is 1 or 2, and wherein one substituent R is benzene, and the other substituent R is an ester group of formula C-34, wherein a is 3, and $R^{11}$ is ethyl, propyl, butyl, pentyl or hexyl ($PCBC_{2-6}$), and preferably $R^{11}$ is hexyl ($PCBC_6$).

The compounds of formula I are easy to synthesize, especially by methods suitable for mass production, and exhibit advantageous properties, for example good structural organization and film-forming properties, good electronic properties, especially high charge carrier mobility, good processability, especially high solubility in organic solvents, and high light and thermal stability.

The compounds of formula I can be synthesized according to or in analogy to methods that are known to the skilled person and are described in the literature. For example, synthesis paths towards various fullerenes of formula I have been previously outlined in literature: J. Mater. Chem., 1997, 7(7), 1097-1109; Chem. Soc. Rev., 1999, 28, 263-277; Chem. Rev. 2013, 113, 5262-5321; J. Am. Chem. Soc. 2011, 133, 2402-2405; and Chem. Rev., 2006, 106(12), 5049-5135.

The compounds of formula I and its subformulae can be used in mixtures, for example together with other monomeric compounds, or polymers, having one or more of a semiconducting, charge transport, hole transport, electron transport, hole blocking, electron blocking, electrically conducting, photoconducting and light emitting property Thus, another aspect of the invention relates to a composition (hereinafter referred to as "fullerene composition"), comprising a mixture comprising one or more compounds of formula I, and further comprising one or more additional compounds, preferably having one or more of a semiconducting, charge transport, hole transport, electron transport, hole blocking, electron blocking, electrically conducting, photoconducting and light emitting property.

The additional compounds in the fullerene composition can be selected for example from fullerene derivatives other than those of this invention, or from conjugated organic polymers.

The fullerene mixture comprising two or more compounds of formula I is especially suitable as electron acceptor or n-type semiconductor, especially in semiconducting materials containing both donor and acceptor components, and for the preparation of a mixture of p-type and n-type semiconductors which are suitable for use in BHJ OPV devices and OPD devices.

In particular for OPV and OPD applications the fullerene mixture comprising two or more compounds of formula I is preferably blended with a further p-type semiconductor such as a polymer, an oligomer or a defined molecular unit to form the active layer in the OPV/OPD device (also referred to as "active layer" or "photoactive layer").

Thus, a preferred embodiment of the present invention relates to a fullerene composition, comprising two or more fullerenes of formula I, and further comprising one or more conjugated organic polymers, which are preferably selected from electron donor, or p-type, semiconducting polymers.

Such a fullerene composition is especially suitable for use in the photoactive layer of an OPV or OPD device. Preferably the fullerene(s) and polymer(s) are selected such that the fullerene composition forms a bulk heterojunction (BHJ).

The OPV/OPD device is usually further composed of a first, transparent or semi-transparent electrode, typically provided on a transparent or semi-transparent substrate, on one side of the active layer, and a second metallic or semi-transparent electrode on the other side of the active layer. Additional interfacial layer(s) acting as hole blocking layer, hole transporting layer, electron blocking layer and/or electron transporting layer, typically comprising a metal oxide (for example, $ZnO_x$, $TiO_x$, ZTO, $MoO_x$, $NiO_x$), a salt (example: LiF, NaF), a conjugated polymer electrolyte (for example: PEDOT:PSS or PFN), a conjugated polymer (for example: PTAA) or an organic compound (for example: NPB, $Alq_3$, TPD), can be inserted between the active layer and an electrode.

A suitable conjugated organic polymer (hereinafter simply referred to as "polymer") for use in a fullerene composition according to the present invention can be selected from polymers as described in prior art, for example in WO/2010/008672, WO/2010/049323, WO 2011/131280, WO/2011/052709, WO/2011/052710, US/2011/0017956, WO/2012/030942 or US/8334456B2.

A preferred polymer is selected from the group consisting of poly(3-substituted thiophene) and poly(3-substituted selenophene), for example poly(3-alkyl thiophene) or poly(3-alkyl selenophene), preferably poly(3-hexyl thiophene) or poly(3-hexyl selenophene).

A further preferred polymer comprises one or more repeating units selected from formulae PIIa and PIIb:

PIIa

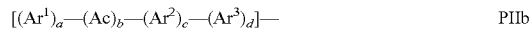

PIIb wherein

Ac is arylene or heteroarylene with 5 to 30 ring atoms that is optionally substituted by one or more groups $R^S$, and preferably has electron acceptor property, D is arylene or heteroarylene with 5 to 30 ring atoms that is different from A, is optionally substituted by one or more groups $R^S$, and preferably has electron donor property, $Ar^1$, $Ar^2$, $Ar^3$ are, on each occurrence identically or differently, and independently of each other, arylene or heteroarylene that is different from A and D, preferably has 5 to 30 ring atoms, and is optionally substituted, preferably by one or more groups $R^P$, $R^P$ is on each occurrence identically or differently F, Br, Cl, —CN, —NC, —NCO, —NCS, —OCN, —SCN, —C(O)NR$^0$R$^{00}$, —C(O)X$^0$, —C(O)R$^0$, —C(O)OR$^0$, —NH$_2$, —NR$^0$R$^{00}$, —SH, —SR$^0$, —SO$_3$H, —SO$_2$R$^0$, —OH, —NO$_2$, —CF$_3$, —SF$_5$, optionally substituted silyl, carbyl or hydrocarbyl with 1 to 40 C atoms that is optionally substituted and optionally comprises one or more hetero atoms, $R^0$ and $R^{00}$ are independently of each other H or optionally substituted $C_{1-40}$ carbyl or hydrocarbyl, and preferably denote H or alkyl with 1 to 12 C-atoms, $X^0$ is halogen, preferably F, Cl or Br, a, b, c are on each occurrence identically or differently 0, 1 or 2, d is on each occurrence identically or differently 0 or an integer from 1 to 10.

Preferably the polymer comprises at least one repeating unit of formula PIIa wherein b is at least 1. Further preferably the polymer comprises at least one repeating unit of formula PIIa wherein b is at least 1, and at least one repeating unit of formula PIIb wherein b is at least 1.

A further preferred polymer comprises, in addition to the units of formula PIIa and/or PIIb, one or more repeating units selected from monocyclic or polycyclic arylene or heteroarylene groups that are optionally substituted.

These additional repeating units are preferably selected of formula PIII

PIII wherein $Ar^1$, $Ar^2$, $Ar^3$, a, c and d are as defined in formula PIIa.

$R^P$ preferably denotes, on each occurrence identically or differently, H, straight-chain, branched or cyclic alkyl with 1 to 30 C atoms, in which one or more CH$_2$ groups are optionally replaced by —O—, —S—, —C(O)—, —C(S)—, —C(O)—O—, —O—C(O)—, —NR$^0$—, —SiR$^0$R$^{00}$—, —CF$_2$—, —CHR$^0$=CR$^{00}$—, —CY$^1$=CY$^2$— or —C≡C— in such a manner that O and/or S atoms are not linked directly to one another, and in which one or more H atoms are optionally replaced by F, Cl, Br, I or CN, or denotes aryl, heteroaryl, aryloxy or heteroaryloxy with 4 to 20 ring atoms which is optionally substituted, preferably by halogen or by one or more of the aforementioned alkyl or cyclic alkyl groups, wherein $R^0$ and $R^{00}$ and $Y^1$ and $Y^2$ have one of the meanings given above and below, $R^0$ and $R^{00}$ preferably denote H or alkyl with 1 to 12 C-atoms, and $Y^1$ and $Y^2$ preferably denote F, Cl or Br.

Further preferably the polymer is selected of formula PIV:

      PIV wherein
A, B, C independently of each other denote a distinct unit of formula PIIa, PIIb or PIII,
x is >0 and ≤1,
y is ≥0 and <1,
z is ≥0 and <1,
x+y+z is 1, and
n1 is an integer >1.

Preferably at least one of B or C denotes a unit of formula PIIa. Very preferably one of B and C denotes a unit of formula PIIa and one of B and C denotes a unit of formula PIIIb.

A preferred polymer of formula PIV is selected from the following formulae

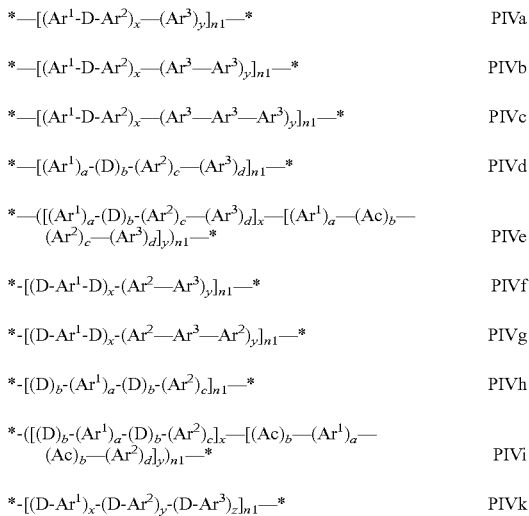

wherein D, $Ar^1$, $Ar^2$, $Ar^3$, a, b, c and d have in each occurrence identically or differently one of the meanings given in formula PIIa, Ac has on each occurrence identically or differently one of the meanings given in formula PIIb, and x, y, z and n1 are as defined in formula PIV, wherein these polymers can be alternating or random copolymers, and wherein in formula PIVd and PIVe in at least one of the repeating units $[(Ar^1)_a\text{-}(D)_b\text{-}(Ar^2)_c\text{—}(Ar^3)_d]$ and in at least one of the repeating units $[(Ar^1)_a\text{—}(Ac)_b\text{—}(Ar^2)_c\text{—}(Ar^3)_d]$ b is at least 1 and wherein in formula PIVh and PIVi in at least one of the repeating units $[(D)_b\text{-}(Ar^1)_a\text{-}(D)_b\text{-}(Ar^2)_d]$ and in at least one of the repeating units $[(D)_b\text{-}(Ar^1)_a\text{-}(D)_b\text{-}(Ar^2)_d]$ b is at least 1.

In the polymers of formula PIV and its subformulae PIVa to PIVk, b is preferably 1 in all repeating units.

In the polymers of formula PIV and its subformulae PIVa to PIVk, x is preferably from 0.1 to 0.9, very preferably from 0.3 to 0.7.

In a preferred embodiment of the present invention one of y and z is 0 and the other is >0. In another preferred embodiment of the present invention, both y and z are 0. In yet another preferred embodiment of the present invention, both y and z are >0. If in the polymers of formula PIV and its subformulae PIVa to PIVk y or z is >0, it is preferably from 0.1 to 0.9, very preferably from 0.3 to 0.7.

In the polymer, the total number of repeating units n1 is preferably from 2 to 10,000. The total number of repeating units n1 is preferably ≥5, very preferably ≥10, most preferably ≥50, and preferably ≤500, very preferably ≤1,000, most preferably ≤2,000, including any combination of the aforementioned lower and upper limits of n1.

The polymer can be a homopolymer or copolymer, like a statistical or random copolymer, alternating copolymer or block copolymer, or a combination of the aforementioned.

Especially preferred is a polymer selected from the following groups:
  Group A consisting of homopolymers of the unit D or $(Ar^1\text{-}D)$ or $(Ar^1\text{-}D\text{-}Ar^2)$ or $(Ar^1\text{-}D\text{-}Ar^3)$ or $(D\text{-}Ar^2\text{—}Ar^3)$ or $(Ar^1\text{-}D\text{-}Ar^2\text{—}Ar^3)$ or $(D\text{-}Ar^1\text{-}D)$, i.e. where all repeating units are identical,
  Group B consisting of random or alternating copolymers formed by identical units $(Ar^1\text{-}D\text{-}Ar^2)$ or $(D\text{-}Ar^1\text{-}D)$ and identical units $(Ar^3)$,
  Group C consisting of random or alternating copolymers formed by identical units $(Ar^1\text{-}D\text{-}Ar^2)$ or $(D\text{-}Ar^1\text{-}D)$ and identical units $(A^1)$,
  Group D consisting of random or alternating copolymers formed by identical units $(Ar^1\text{-}D\text{-}Ar^2)$ or $(D\text{-}Ar^1\text{-}D)$ and identical units $(Ar^1\text{—}Ac\text{—}Ar^2)$ or $(Ac\text{—}Ar^1\text{—}Ac)$, wherein in all these groups D, Ac, $Ar^1$, $Ar^2$ and $Ar^3$ are as defined above and below, in groups A, B and C $Ar^1$, $Ar^2$ and $Ar^3$ are different from a single bond, and in group D one of $Ar^1$ and $Ar^2$ may also denote a single bond.

A preferred polymer of formula PIV and PIVa to PIVk is selected of formula PV

      PV wherein "chain" denotes a polymer chain of formulae PIV or PIVa to PIVk, and $R^{21}$ and $R^{22}$ have independently of each other one of the meanings of $R^S$ as defined above, or denote, independently of each other, H, F, Br, Cl, I, —CH$_2$Cl, —CHO, —CR'=CR''$_2$, —SiR'R''R''', —SiR'X'X'', —SiR'R''X', —SnR'R''R''', BR'R'', —B(OR')(OR''), —B(OH)$_2$, —O—SO$_2$—R', —C≡CH, —C≡C—SiR'$_3$, —ZnX' or an endcap group, X' and X'' denote halogen, R', R'' and R''' have independently of each other one of the meanings of $R^0$ given in formula I, and two of R', R'' and R''' may also form a cyclosilyl, cyclostannyl, cycloborane or cycloboronate group with 2 to 20 C atoms together with the respective hetero atom to which they are attached.

Preferred endcap groups $R^{21}$ and $R^{22}$ are H, $C_{1\text{-}20}$ alkyl, or optionally substituted $C_{6\text{-}12}$ aryl or $C_{2\text{-}10}$ heteroaryl, very preferably H or phenyl.

In the polymer represented by formula PIV, PIVa to PIVk or PV, x, y and z denote the mole fraction of units A, B and C, respectively, and n denotes the degree of polymerisation or total number of units A, B and C. These formulae includes block copolymers, random or statistical copolymers and alternating copolymers of A, B and C, as well as homopolymers of A for the case when x>0 and y=z=0.

In the repeating units and polymers of formulae PIIa, PIIb, PIII, PIV, PIVa-PIVk and PV, preferably D, $Ar^1$, $Ar^2$ and $Ar^3$ are selected from the group consisting of the following formulae

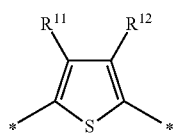 (D1)
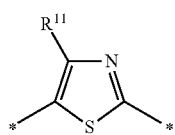 (D2)
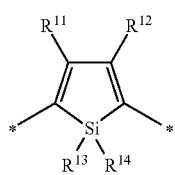 (D3)
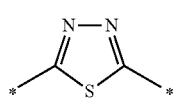 (D4)
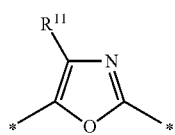 (D5)
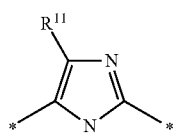 (D6)
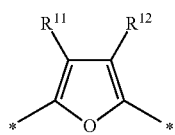 (D7)
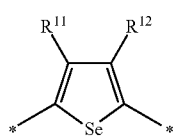 (D8)
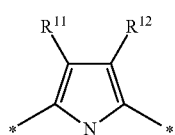 (D9)
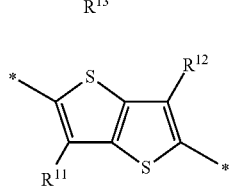 (D10)
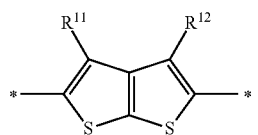 (D11)
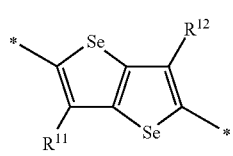 (D12)
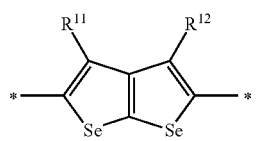 (D13)
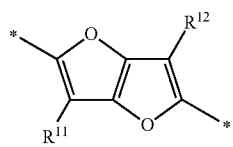 (D14)
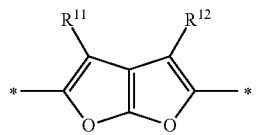 (D15)
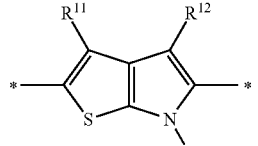 (D16)
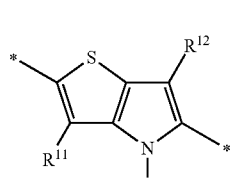 (D17)
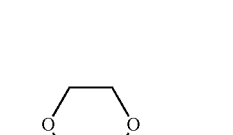 (D18)
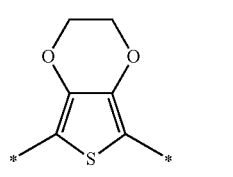 
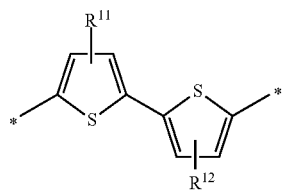 (D19)

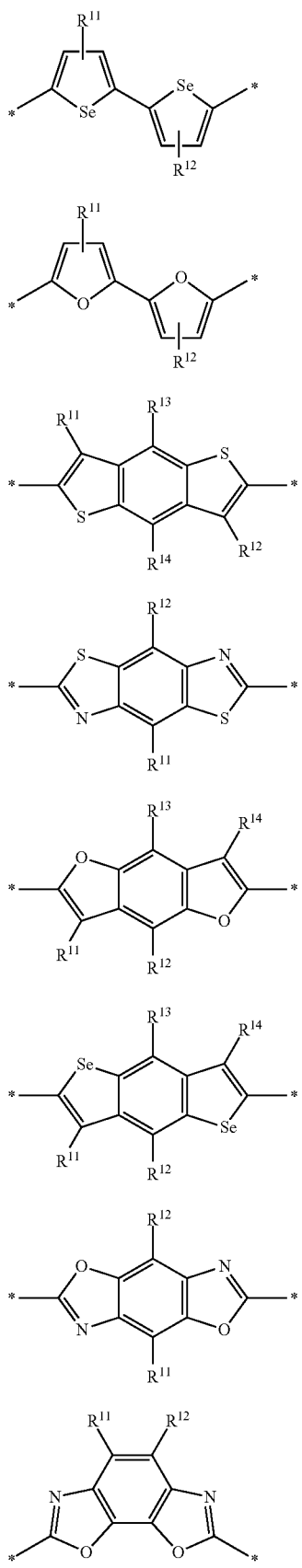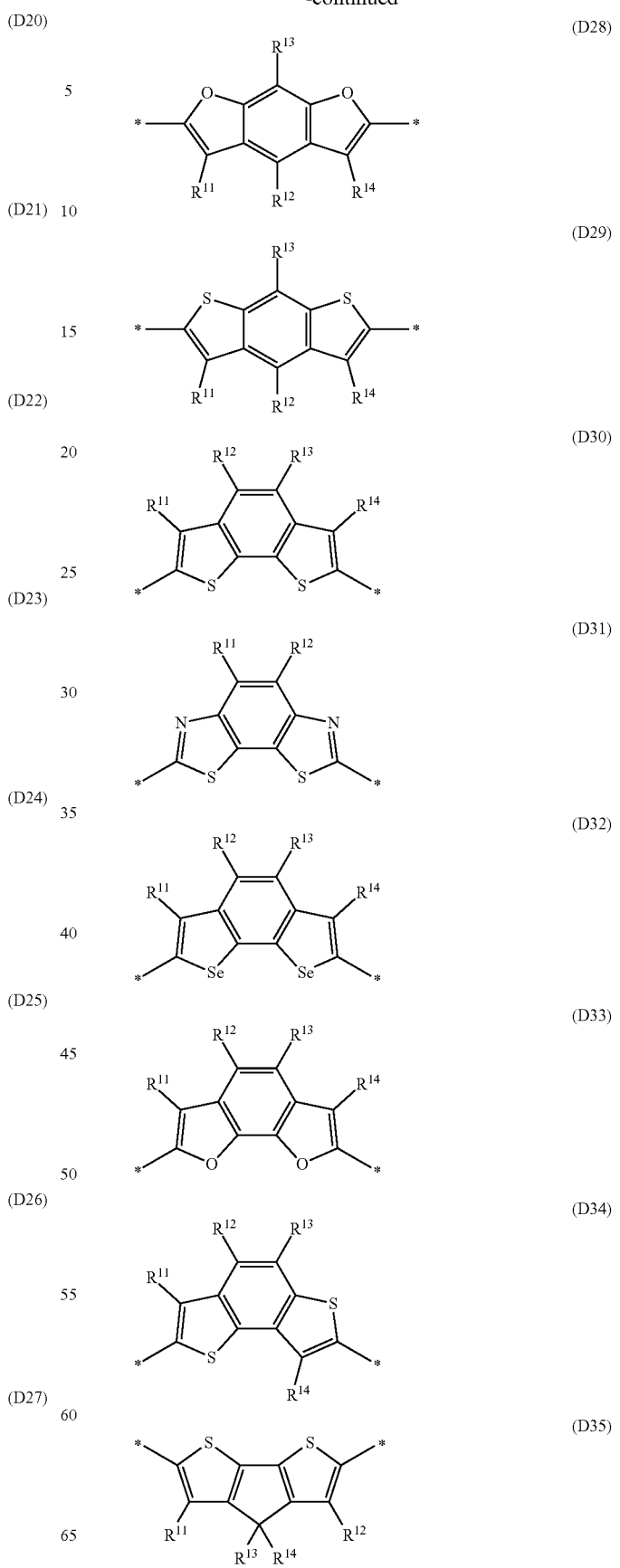

(D36)
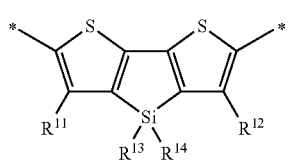
(D37)
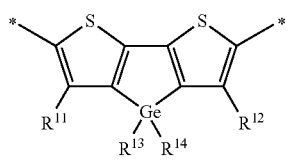
(D38)
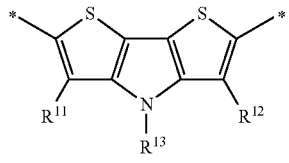
(D39)
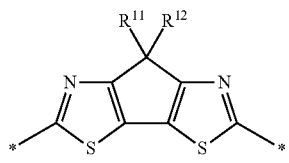
(D40)
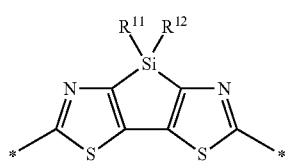
(D41)
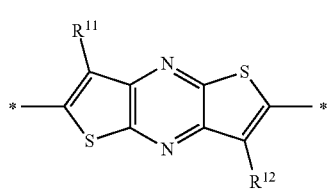
(D42)
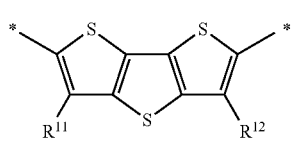
(D43)
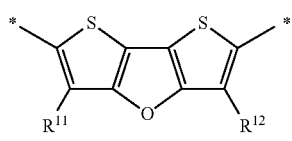
(D44)
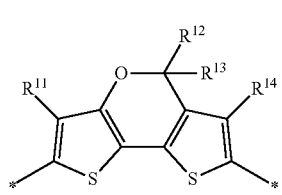
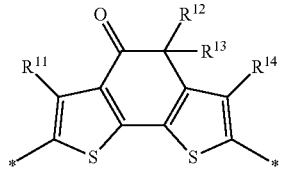
(D45)
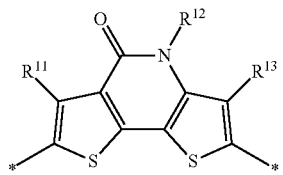
(D46)
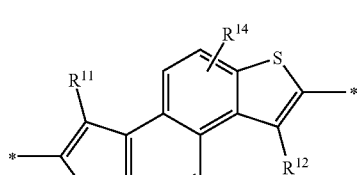
(D47)
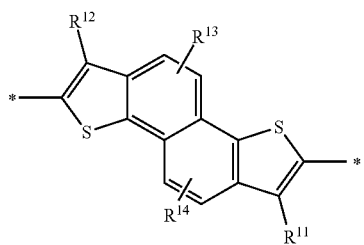
(D48)
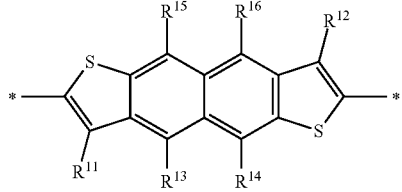
(D49)
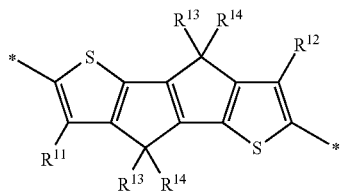
(D50)
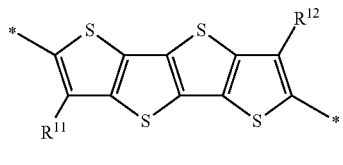
(D51)
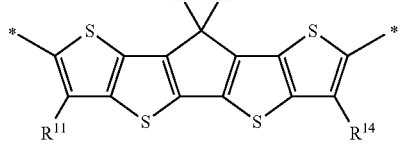
(D52)

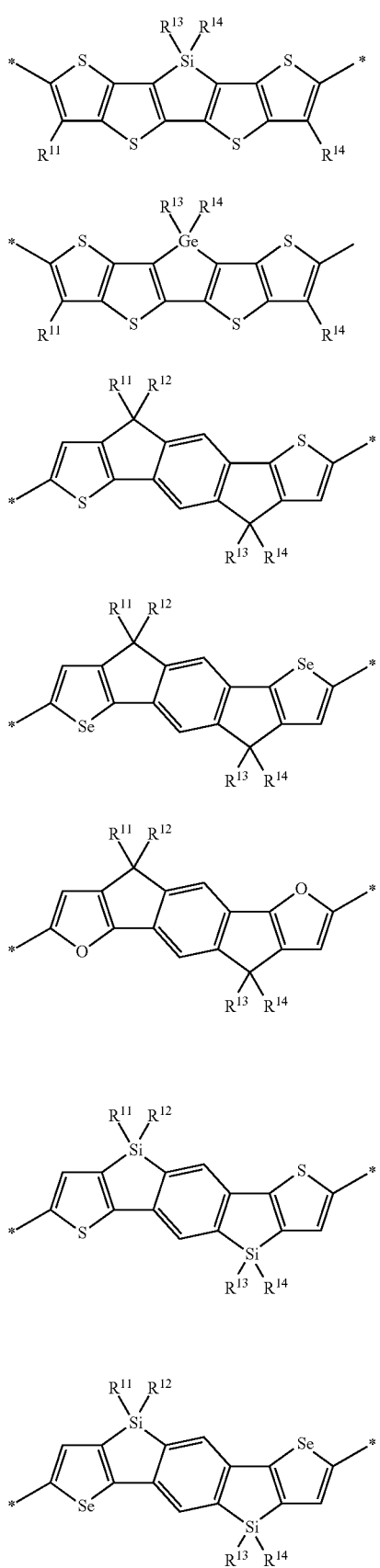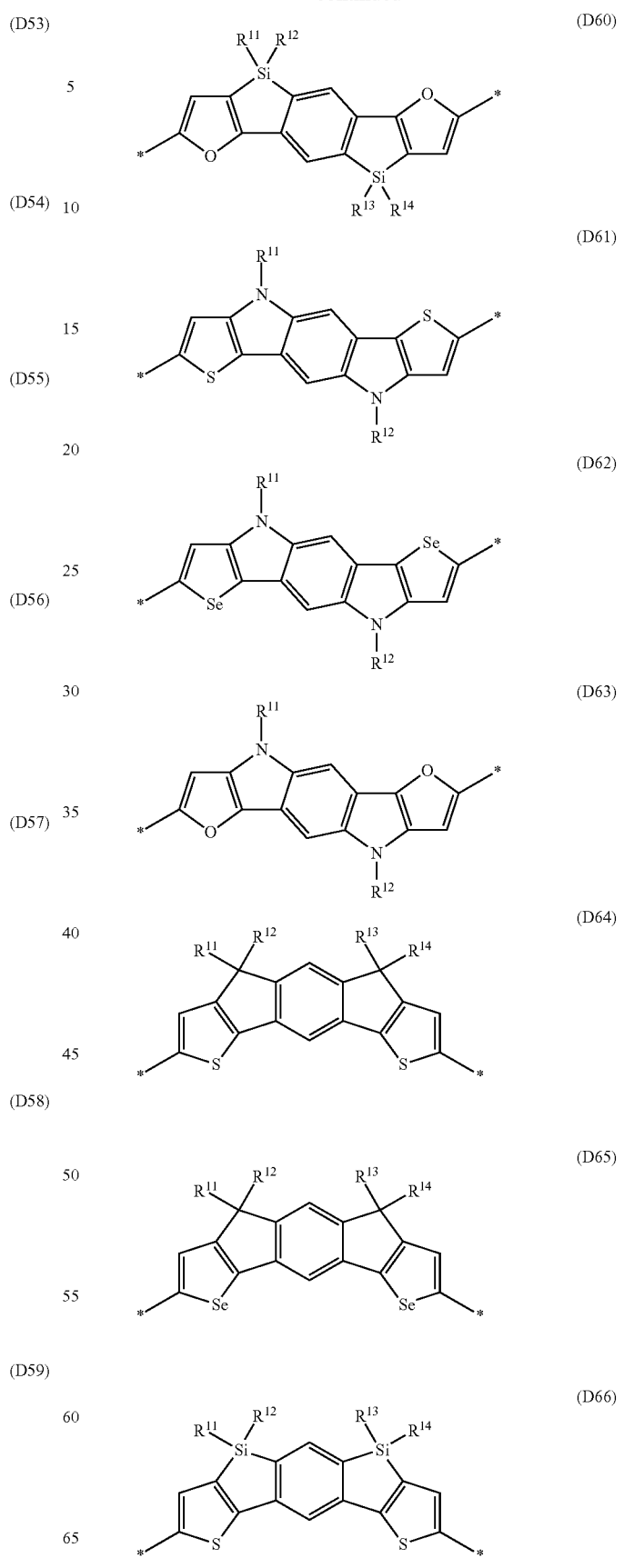

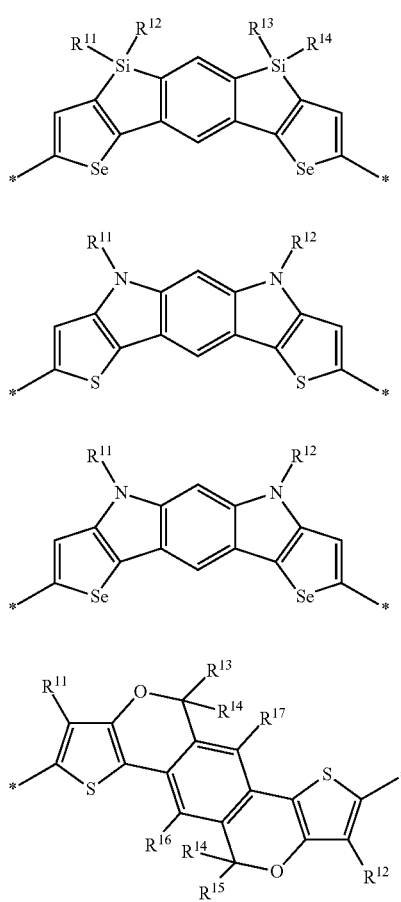
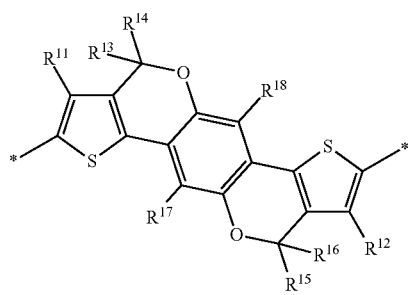
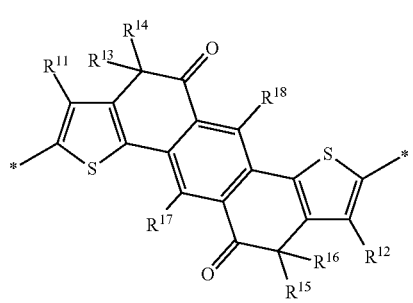
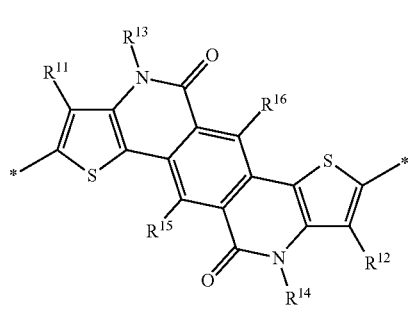
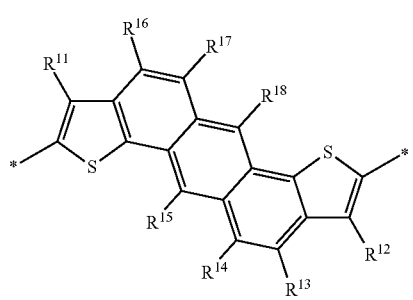
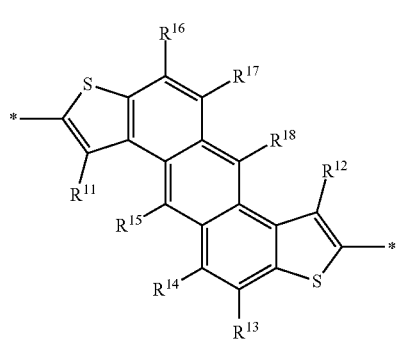

(D78) 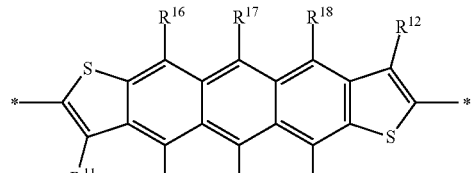
(D79) 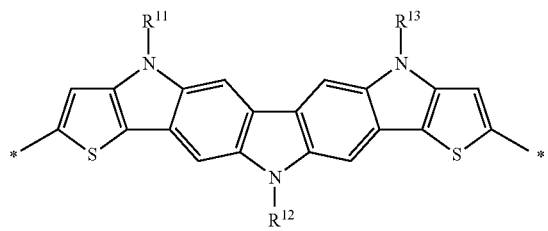
(D80) 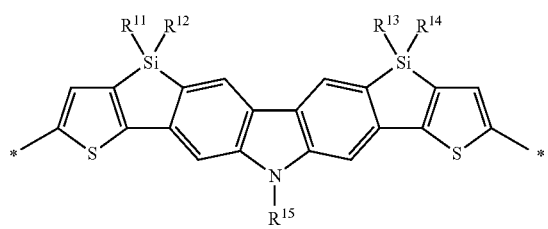
(D81) 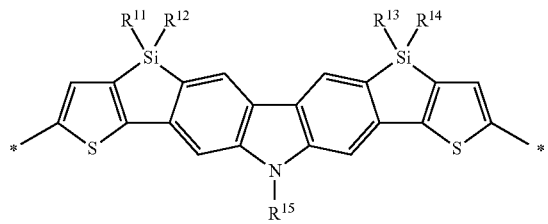
(D82) 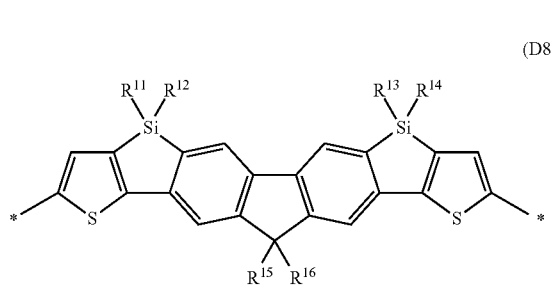
(D83) 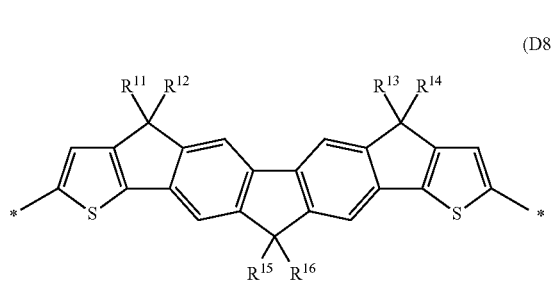
(D84) 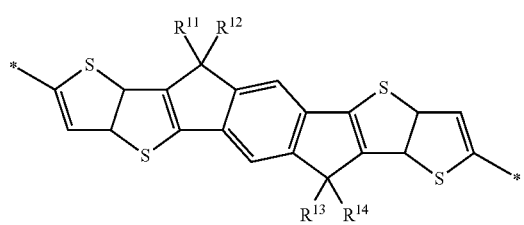
(D85) 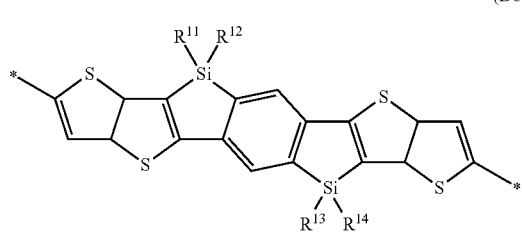
(D86) 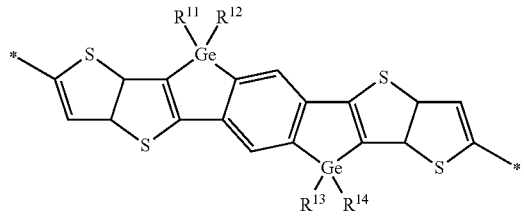
(D87) 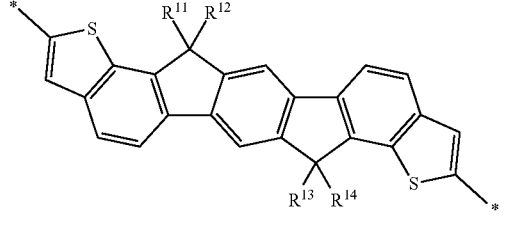
(D88) 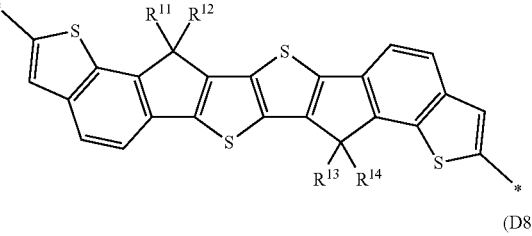
(D89) 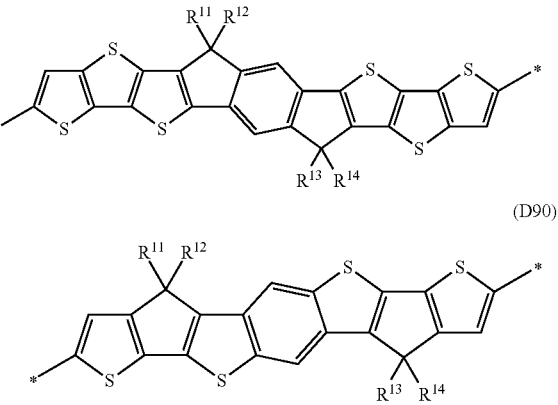
(D90)

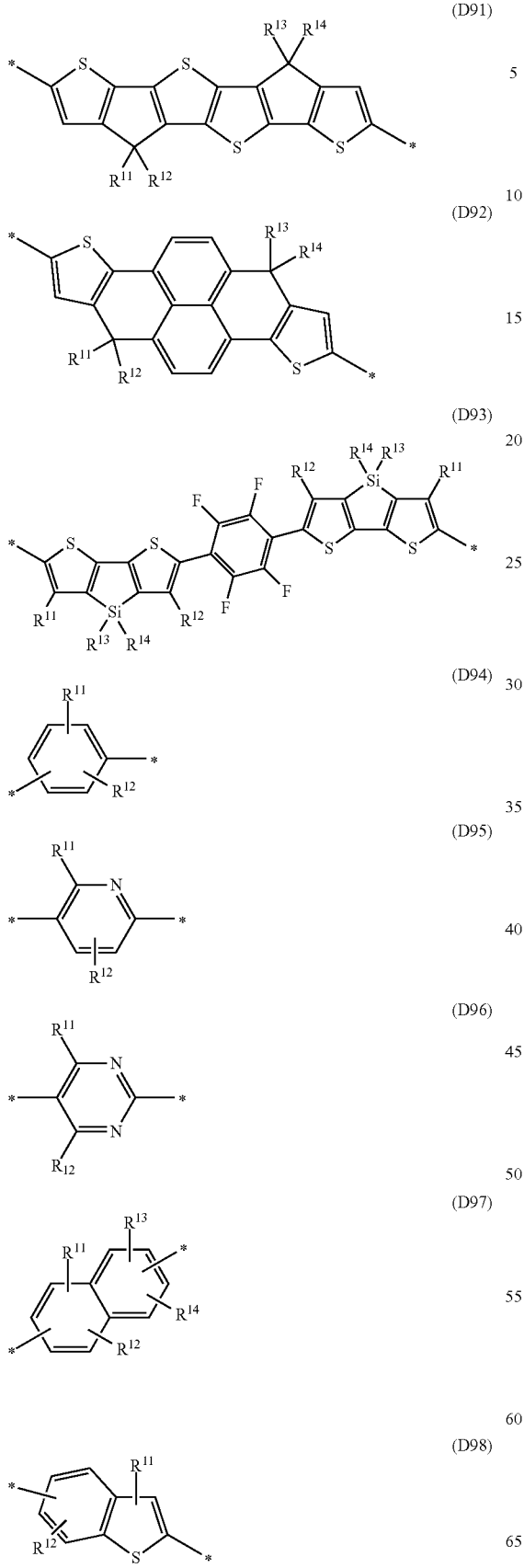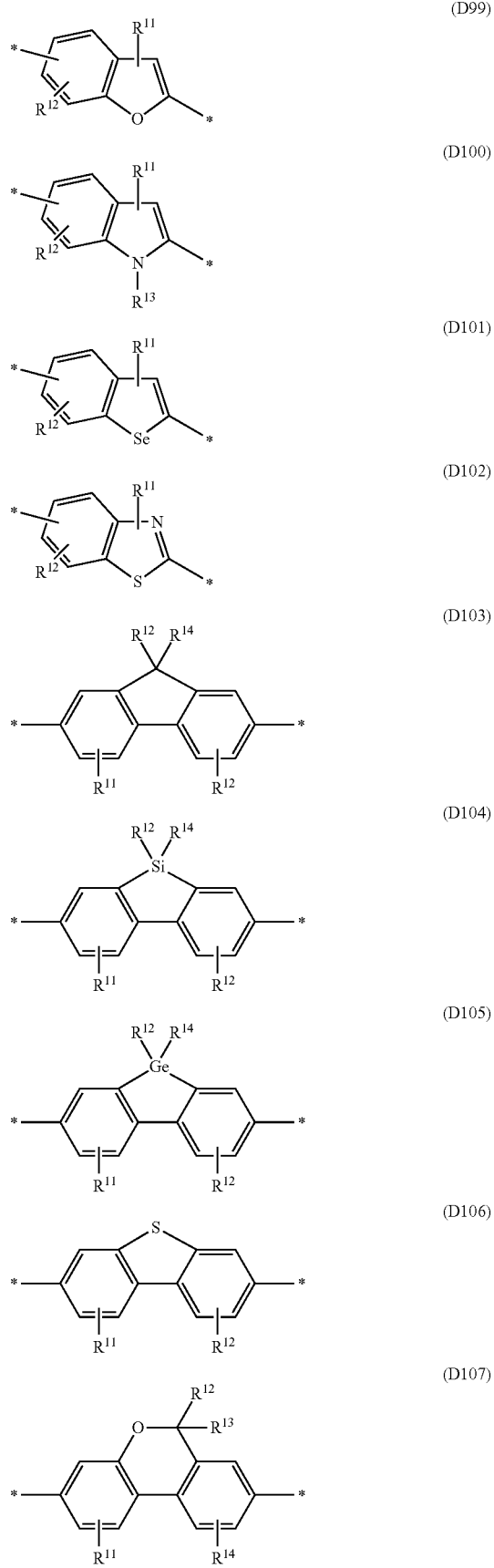

-continued
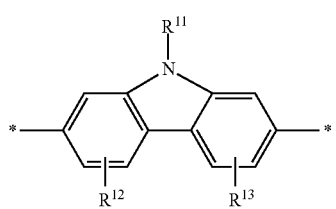
(D108)
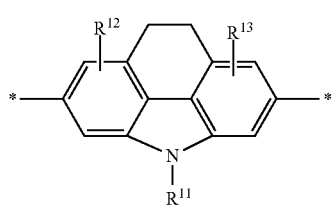
(D109)
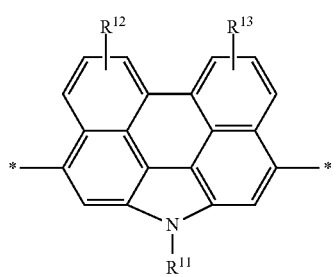
(D110)
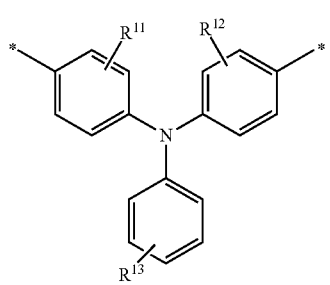
(D111)
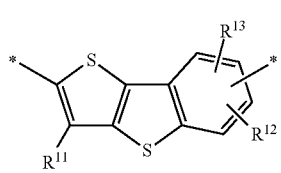
(D112)
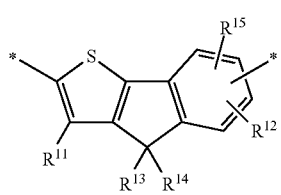
(D113)
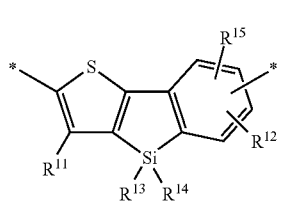
(D114)
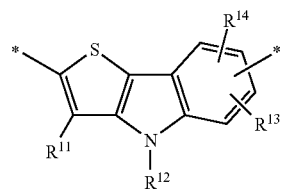
(D115)
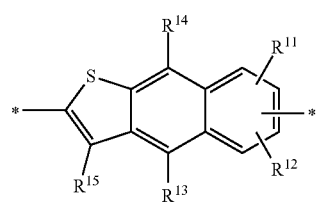
(D116)
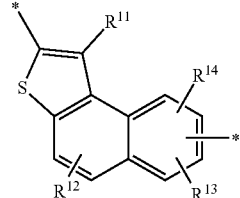
(D117)
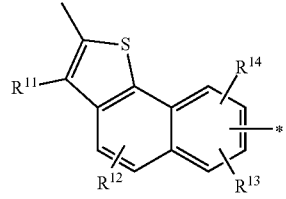
(D118)
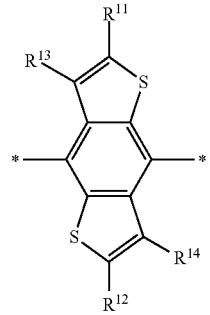
(D119)
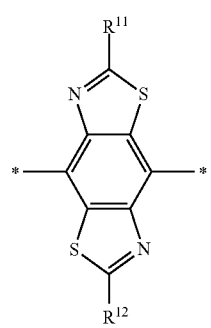
(D120)

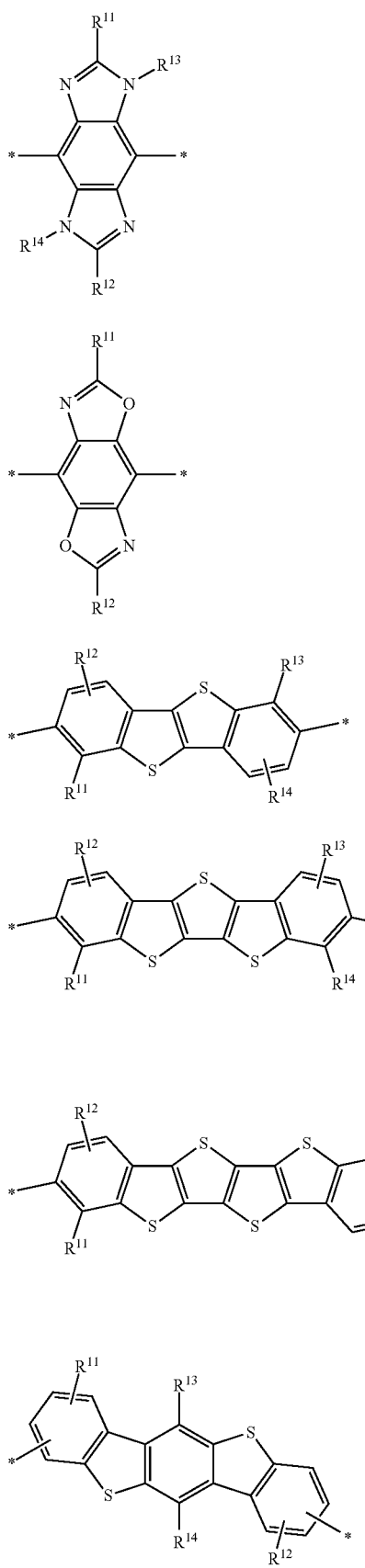
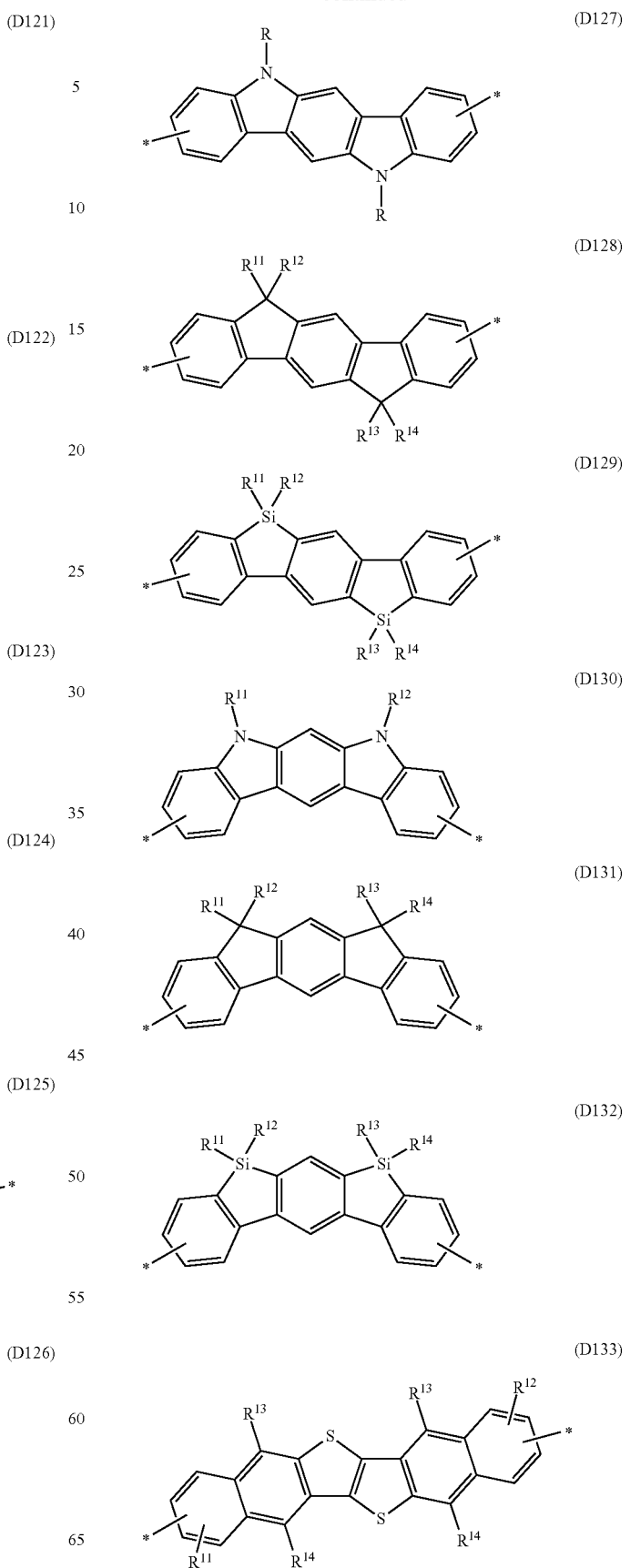

-continued (D134)
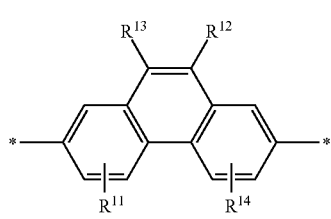

(D135)
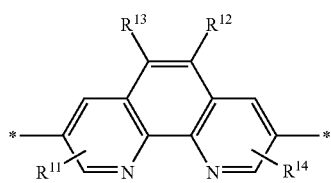

(D136)
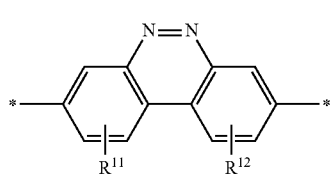

(D137)
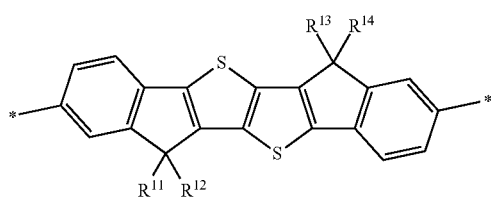

(D138)
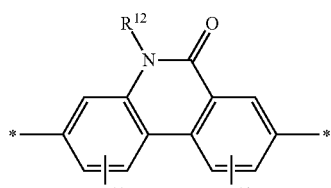

(D139)
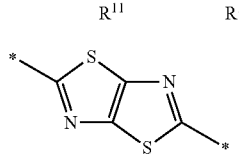

(D140)
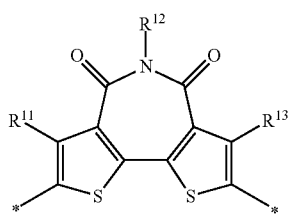

(D141)
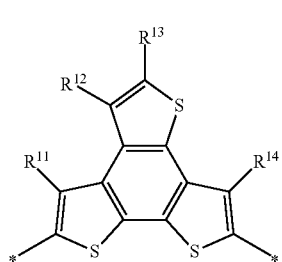

wherein $R^{11}$, $R^{12}$, $R^{13}$, $R^{14}$, $R^{15}$, $R^{16}$, $R^{17}$ and $R^{18}$ independently of each other denote H or have one of the meanings of $R^P$ as defined above and below.

In the repeating units and polymers of formulae PIIa, PIIb, PIII, PIV, PIVa-PIVk and PV, preferably Ac, $Ar^1$, $Ar^2$ and $Ar^3$ are selected from the group consisting of the following formulae (A1)
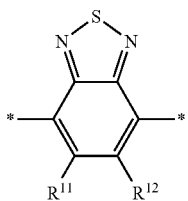

(A2)
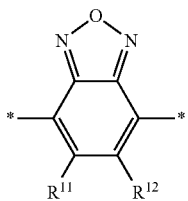

(A3)
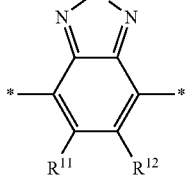

(A4)
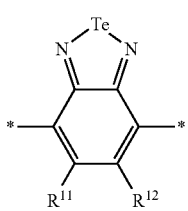

(A5)
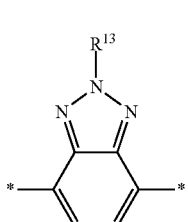

(A6)
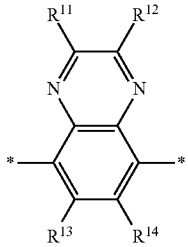

-continued
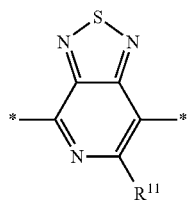
(A7)
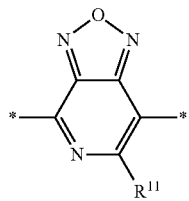
(A8)
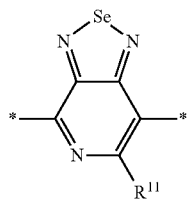
(A9)
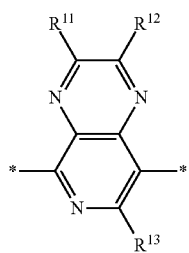
(A10)
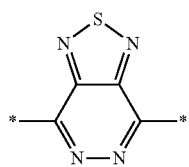
(A11)
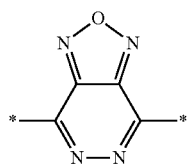
(A12)
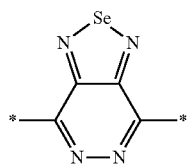
(A13)
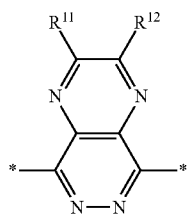
(A14)
-continued
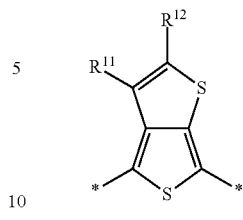
(A15)
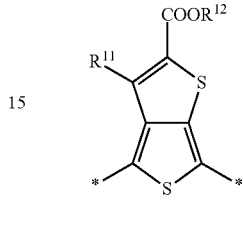
(A16)
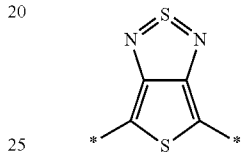
(A17)
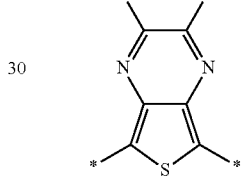
(A18)
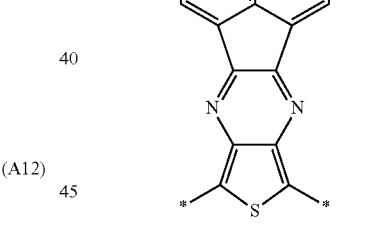
(A19)
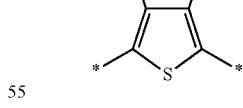
(A20)
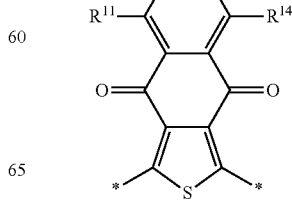
(A21)

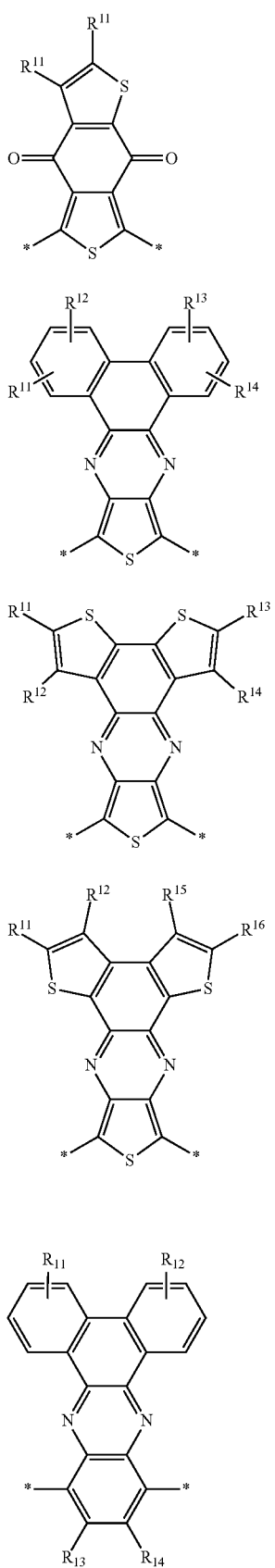
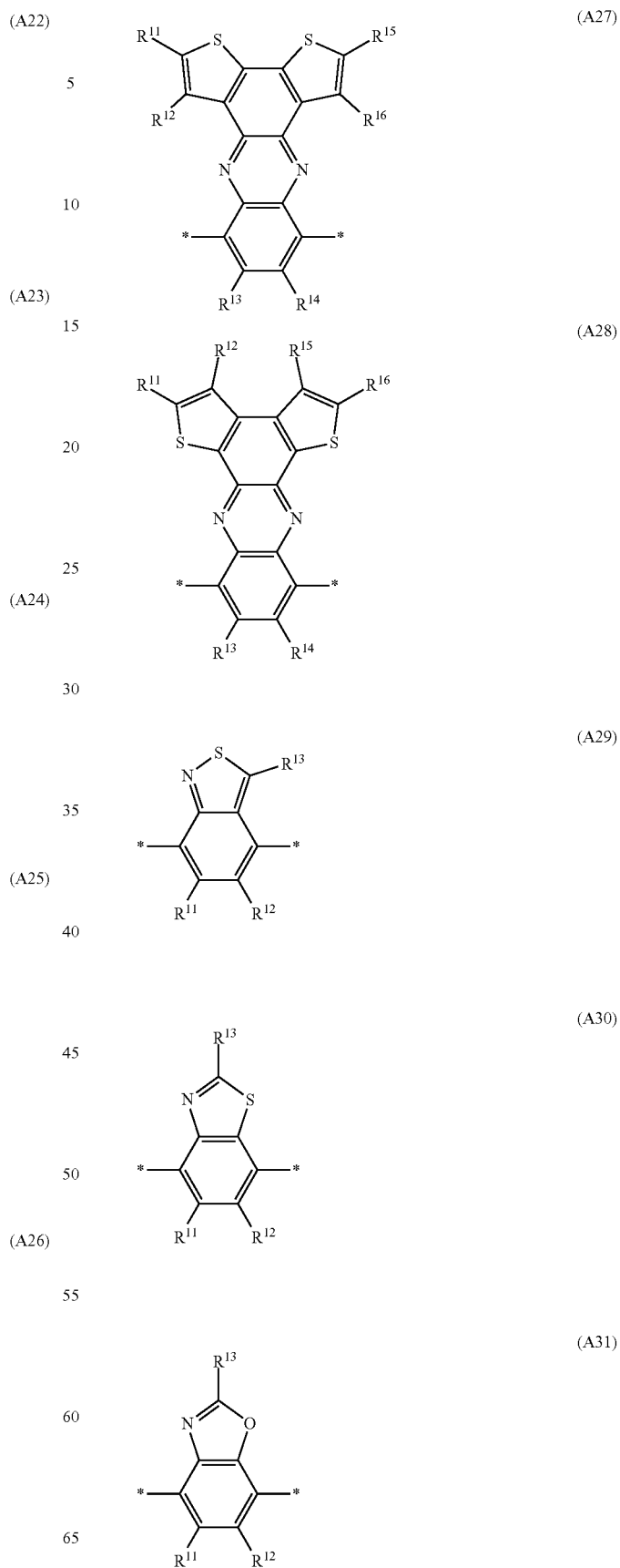

-continued
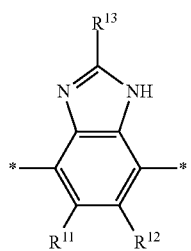 (A32)
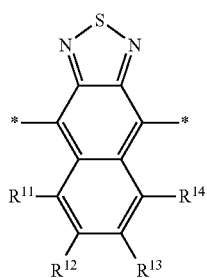 (A33)
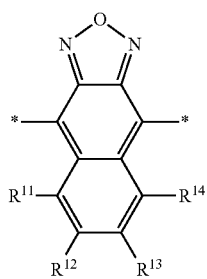 (A34)
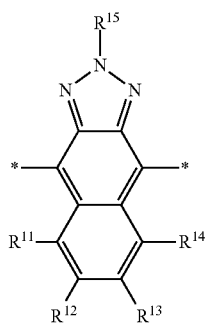 (A35)
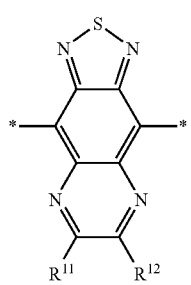 (A36)
-continued
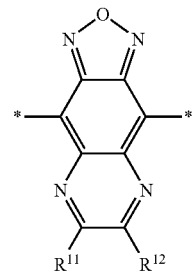 (A37)
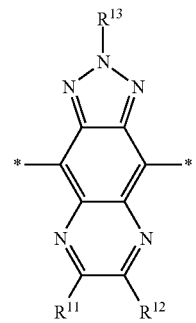 (A38)
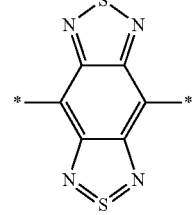 (A39)
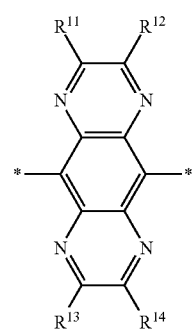 (A40)
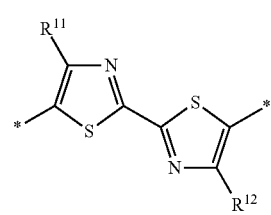 (A41)
(A42)
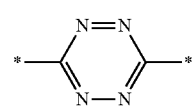 (A43)

(A44) 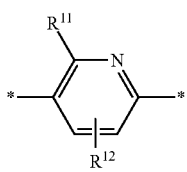
(A45) 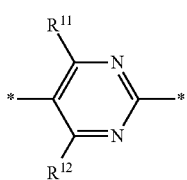
(A46) 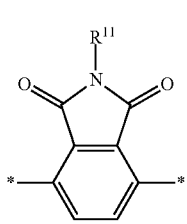
(A47) 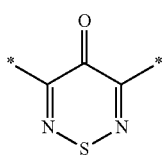
(A48) 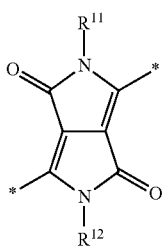
(A49) 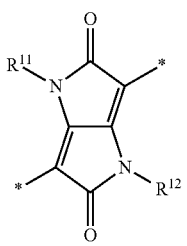
(A50) 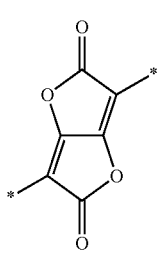
(A51) 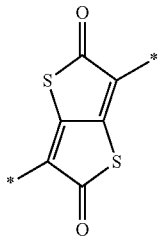
(A52) 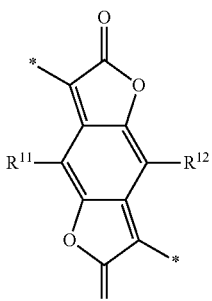
(A53) 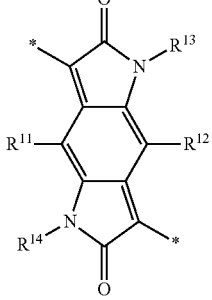
(A54) 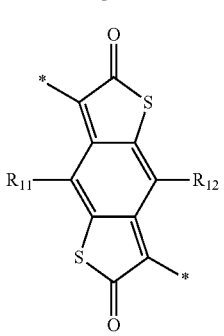
(A55) 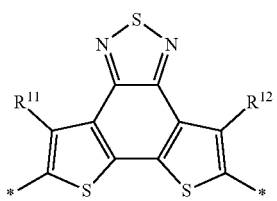
(A56) 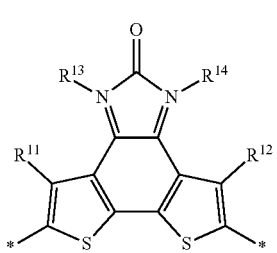

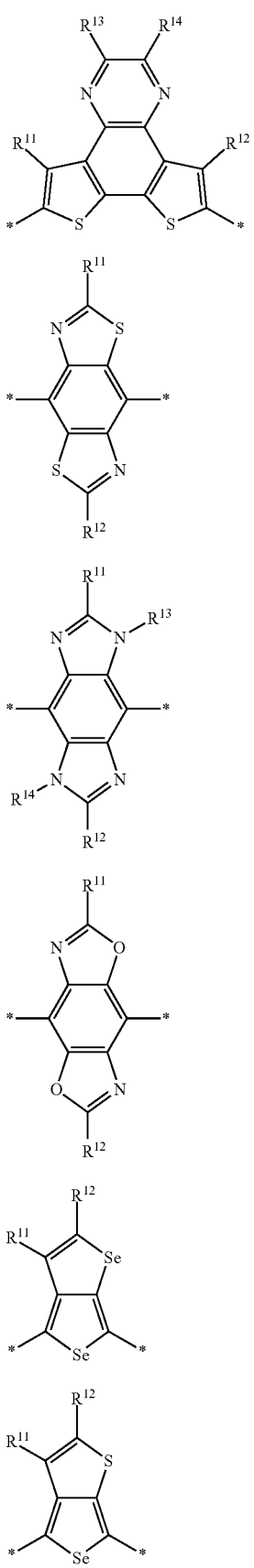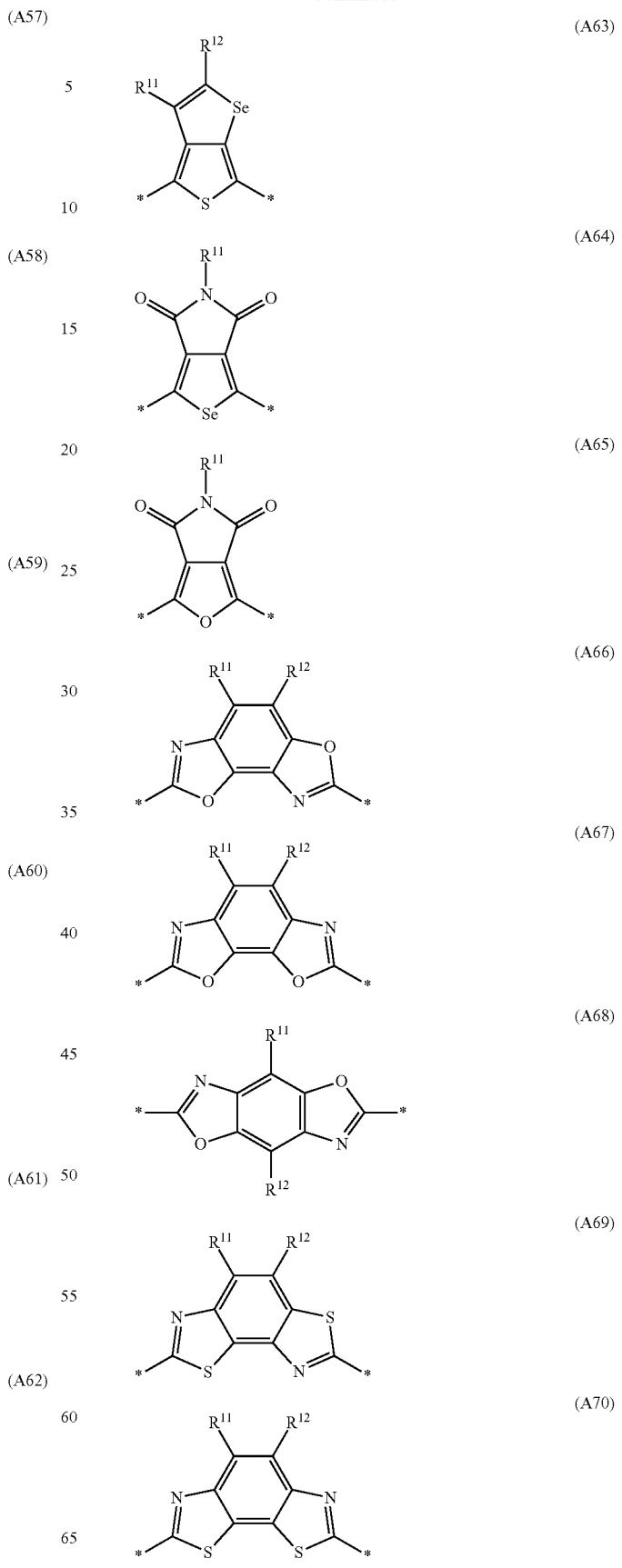

-continued
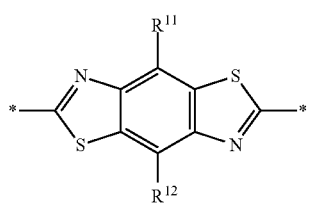
(A71)
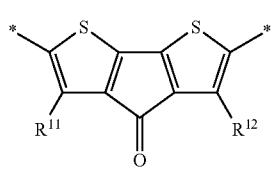
(A72)
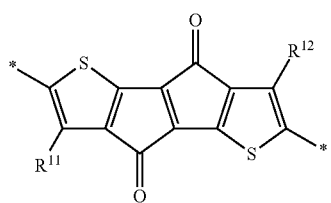
(A73)
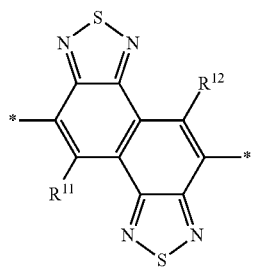
(A74)
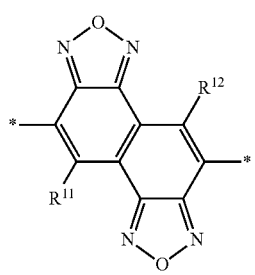
(A75)
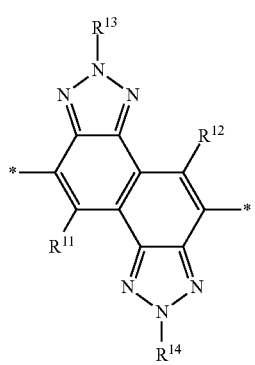
(A76)
-continued
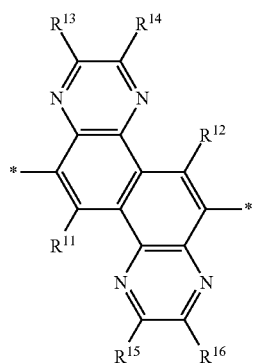
(A77)
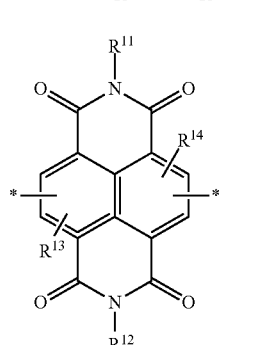
(A78)
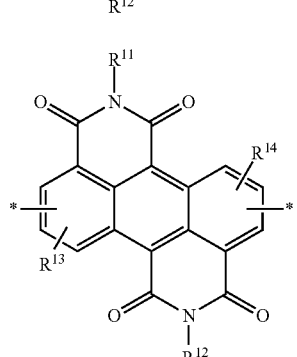
(A79)
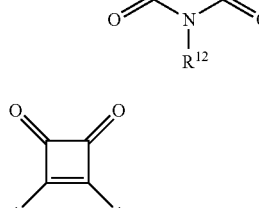
(A80)
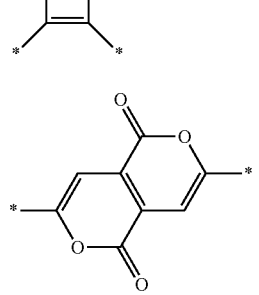
(A81)
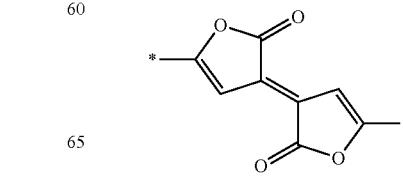
(A82)

-continued
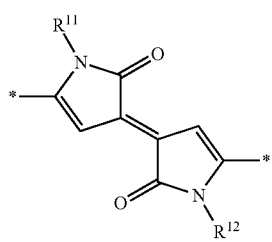
(A83)
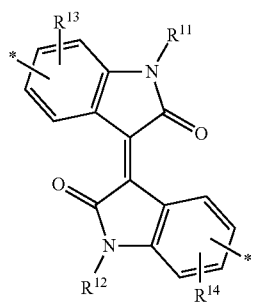
(A84)
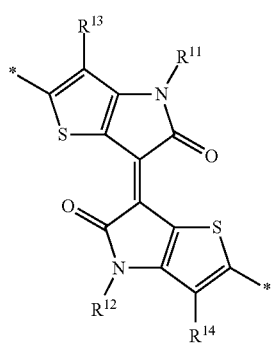
(A85)
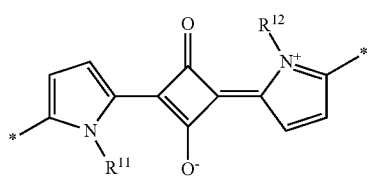
(A86)
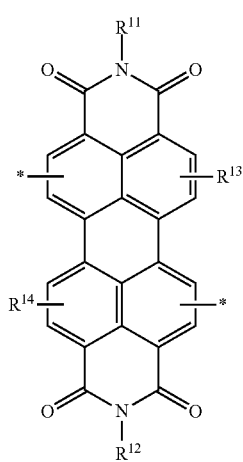
(A87)
-continued
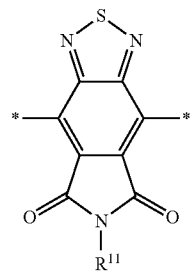
(A88)
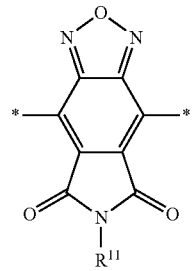
(A89)
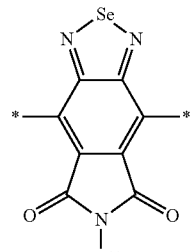
(A90)
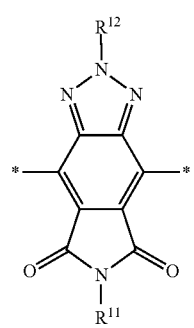
(A91)
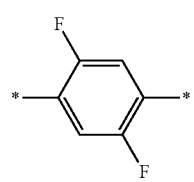
(A92)
(A93)

-continued

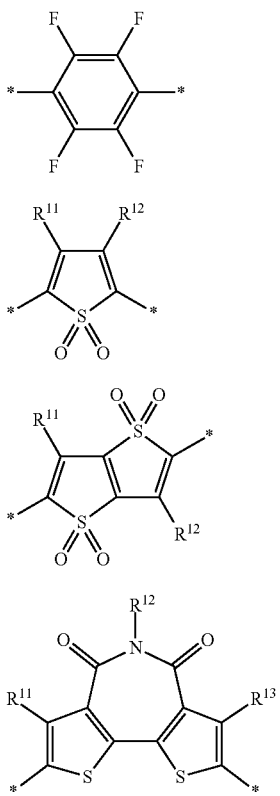

wherein $R^{11}$, $R^{12}$, $R^{13}$, $R^{14}$, $R^{15}$ and $R^{16}$ independently of each other denote H or have one of the meanings of $R^P$ as defined above and below.

The polymer can be prepared for example from monomers selected from the following formulae

| | |
|---|---|
| $R^{23}$—$(Ar^1)_a$-D-$(Ar^2)_c$—$R^{24}$ | PVIa |
| $R^{23}$-D-$(Ar^1)_a$-D-$R^{24}$ | PVIb |
| $R^{23}$—$(Ar^1)_a$—Ac—$(Ar^2)_c$—$R^{24}$ | PVIc |
| $R^{23}$—Ac—$(Ar^1)_a$—Ac—$R^{24}$ | PVId |
| $R^{23}$—$(Ar^1)_a$—$(Ar^2)_c$—$R^{24}$ | PVIe | wherein Ac, D, $Ar^1$, $Ar^2$, a and b have the meanings of formula PIIa and PIIb, or one of the preferred meanings as described above and below, and $R^{23}$ and $R^{24}$ are, preferably independently of each other, selected from the group consisting of H, Cl, Br, I, O-tosylate, O-triflate, O-mesylate, O-nona-flate, —SiMe$_2$F, —SiMeF$_2$, —O—SO$_2$Z$^1$, —B(OZ$^2$)$_2$, —CZ$^3$=C(Z$^3$)$_2$, —C≡CH, —C≡CSi(Z$^1$)$_3$, —ZnX$^0$ and —Sn(Z$^4$)$_3$, wherein X$^0$ is halogen, preferably Cl, Br or I, Z$^{1-4}$ are selected from the group consisting of alkyl and aryl, each being optionally substituted, and two groups Z$^2$ may also together form a cycloboronate group with 2 to 20 C atoms together with the B and O atoms.

Suitable monomers are for example selected from the following subformulae

| | |
|---|---|
| $R^{23}$—$Ar^1$-D-$Ar^2$—$R^{24}$ | PVIa1 |
| $R^{23}$-D-$R^{24}$ | PVIa2 |
| $R^{23}$—$Ar^1$-D-$R^{24}$ | PVIa3 |
| $R^{23}$-D-$Ar^2$—$R^{24}$ | PVIa4 |
| $R^{23}$-D-$Ar^1$-D-$R^{24}$ | PVIb1 |
| $R^{23}$—$Ar^1$—Ac—$Ar^2$—$R^{24}$ | PVIc1 |
| $R^{23}$—Ac—$R^{24}$ | PVIc2 |
| $R^{23}$—$Ar^1$—Ac—$R^{24}$ | PVIc3 |
| $R^{23}$—Ac—$Ar^2$—$R^{24}$ | PVIc4 |
| $R^{23}$—Ac—$Ar^1$—Ac—$R^{24}$ | PVId1 |
| $R^{23}$—$Ar^1$—$R^{24}$ | PVIe1 |
| $R^{23}$—$Ar^1$—$Ar^2$—$R^{24}$ | PVIe2 | wherein Ac, D, $Ar^1$, $Ar^2$, a, c, $R^{23}$ and $R^{24}$ are as defined in formulae PVIa-PVId.

The polymer can be synthesized according to or in analogy to methods that are known to the skilled person and are described in the literature. Other methods of preparation can be taken from the examples. For example, the polymers can be suitably prepared by aryl-aryl coupling reactions, such as Yamamoto coupling, Suzuki coupling, Stille coupling, Sonogashira coupling, C—H activation coupling, Heck coupling or Buchwald coupling. Suzuki coupling, Stille coupling and Yamamoto coupling are especially preferred. The monomers which are polymerised to form the repeat units of the polymers can be prepared according to methods which are known to the person skilled in the art.

For example the polymer can be prepared by coupling one or more monomers selected from formulae PVIa-PVId and their subformulae in an aryl-aryl coupling reaction, wherein $R^{23}$ and $R^{24}$ are selected from Cl, Br, I, —B(OZ$^2$)$_2$ and —Sn(Z$^4$)$_3$.

Preferred aryl-aryl coupling and polymerisation methods used in the processes described above and below are Yamamoto coupling, Kumada coupling, Negishi coupling, Suzuki coupling, Stille coupling, Sonogashira coupling, Heck coupling, C—H activation coupling, Ullmann coupling or Buchwald coupling. Especially preferred are Suzuki coupling, Negishi coupling, Stille coupling and Yamamoto coupling. Suzuki coupling is described for example in WO 00/53656 A1. Negishi coupling is described for example in *J. Chem. Soc., Chem. Commun.*, 1977, 683-684. Yamamoto coupling is described in for example in T. Yamamoto et al., *Prog. Polym. Sci.*, 1993, 17, 1153-1205, or WO 2004/022626 A1, and Stille coupling is described for example in Z. Bao et al., *J. Am. Chem. Soc.*, 1995, 117, 12426-12435. For example, when using Yamamoto coupling, monomers having two reactive halide groups are preferably used. When using Suzuki coupling, monomers of formulae PVIa-PVId and their subformulae having two reactive boronic acid or boronic acid ester groups or two reactive halide groups are preferably used. When using Stille coupling, monomers having two reactive stannane groups or two reactive halide groups are preferably used. When using Negishi coupling, monomers having two reactive organozinc groups or two reactive halide groups are preferably used.

Preferred catalysts, especially for Suzuki, Negishi or Stille coupling, are selected from Pd(0) complexes or Pd(II) salts. Preferred Pd(0) complexes are those bearing at least one phosphine ligand such as Pd(Ph$_3$P)$_4$. Another preferred phosphine ligand is tris(ortho-tolyl)phosphine, i.e. Pd(o-Tol$_3$P)$_4$. Preferred Pd(II) salts include palladium acetate, i.e. Pd(OAc)$_2$. Alternatively the Pd(0) complex can be prepared by mixing a Pd(0) dibenzylideneacetone complex, for example tris(dibenzyl-ideneacetone)dipalladium(0), bis(dibenzylideneacetone)-palladium(0), or Pd(II) salts e.g. palladium acetate, with a phosphine ligand, for example triphenylphosphine, tris(ortho-tolyl)phosphine or tri(tert-butyl)phosphine. Suzuki polymerisation is performed in the presence of a base, for example sodium carbonate, potassium carbonate, lithium hydroxide, potassium phosphate or an organic base such as tetraethylammonium carbonate or tetraethylammonium hydroxide. Yamamoto polymerisation employs a Ni(0) complex, for example bis(1,5-cyclooctadienyl) nickel(0).

Suzuki and Stille polymerisation may be used to prepare homopolymers as well as statistical, alternating and block random copolymers. Statistical or block copolymers can be prepared for example from the above monomers of formula PVI or its subformulae, wherein one of the reactive groups is halogen and the other reactive group is a boronic acid, boronic acid derivative group or and alkylstannane. The synthesis of statistical, alternating and block copolymers is described in detail for example in WO 03/048225 A2 or WO 2005/014688 A2.

The concentration of the fullerene derivatives of this invention, or of the fullerene composition, in a formulation according to the present invention, including solvents, is preferably 0.1 to 10% by weight, more preferably 0.5 to 5% by weight. The concentration of the fullerene derivatives of this invention in a composition comprising a fullerene derivative and a polymer according to the present invention (i.e. excluding solvents), is preferably from 10 to 90% by weight, very preferably from 33% to 80% by weight.

Another aspect of the present invention relates to a formulation comprising one or more fullerene derivatives of this invention or a fullerene composition as described above, and further comprising one or more solvents, preferably selected from organic solvents.

Such a formulation is preferably used as a carrier for the preparation of a semiconducting layer of an OE device, like an OPV or OPD device, wherein the fullerene derivative or fullerene composition is for example used in the photoactive layer.

Optionally, the formulation further comprises one or more binders to adjust the rheological properties, as described for example in WO 2005/055248 A1.

The formulations according to the present invention preferably form a solution.

The invention additionally provides an electronic device comprising a fullerene derivative of this invention or fullerene composition, or a semiconducting layer comprising it, as described above and below.

Especially preferred devices are OFETs, TFTs, ICs, logic circuits, capacitors, RFID tags, OLEDs, OLETs, OPEDs, OPVs, OPDs, solar cells, laser diodes, photoconductors, photodetectors, electrophotographic devices, electrophotographic recording devices, organic memory devices, sensor devices, charge injection layers, Schottky diodes, planarising layers, antistatic films, conducting substrates and conducting patterns.

Especially preferred electronic device are OFETs, OLEDs, OPV and OPD devices, in particular bulk heterojunction (BHJ) OPV devices and OPD devices. In an OFET, for example, the active semiconductor channel between the drain and source may comprise the layer of the invention. As another example, in an OLED device, the charge (hole or electron) injection or transport layer may comprise the layer of the invention.

For use in OPV or OPD devices, preferably a fullerene composition is used that contains a p-type (electron donor) semiconductor and an n-type (electron acceptor) semiconductor. The p-type semiconductor is for example a conjugated polymer having repeating units of formulae PIIa, PIIb or PIII, or a polymer of formula PIV, PV or their subformulae, as shown above, a small molecules, a mixture of a two or more polymers or mixture of one or more polymers and one or more small molecules. The n-type semiconductor is a fullerene derivative of this invention, a mixture of two or more fullerenes, at least one of which is a fullerene derivative of this invention.

The device preferably further comprises a first transparent or semi-transparent electrode on a transparent or semi-transparent substrate on one side of the active layer, and a second metallic or semi-transparent electrode on the other side of the active layer.

Preferably, the active layer according to the present invention is further blended with additional organic and inorganic compounds to enhance the device properties. For example, metal particles such as Au or Ag nanoparticules or Au or Ag nanoprism for enhancements in light harvesting due to near-field effects (i.e. plasmonic effect) as described, for example in Adv. Mater. 2013, 25 (17), 2385-2396 and Adv. Ener. Mater. 10.1002/aenm.201400206, a molecular dopant such as 2,3,5,6-tetrafluoro-7,7,8,8-tetracyanoquinodimethane for enhancement in photoconductivity as described, for example in Adv. Mater. 2013, 25(48), 7038-7044, or a stabilising agent consisting of a UV absorption agent and/or anti-radical agent and/or antioxidant agent such as 2-hydroxybenzophenone, 2-hydroxyphenylbenzotriazole, oxalic acid anilides, hydroxyphenyl triazines, merocyanines, hindered phenol, N-aryl-thiomorpholine, N-aryl-thiomorpholine-1-oxide, N-aryl-thiomorpholine-1,1-dioxide, N-aryl-thiazolidine, N-aryl-thiazolidine-1-oxide, N-aryl-thiazolidine-1,1-dioxide and 1,4-diazabicyclo[2.2.2]octane as described, for example, in WO2012095796 A1 and in WO2013021971 A1.

The device preferably may further comprise a UV to visible photo-conversion layer such as described, for example, in J. Mater. Chem. 2011, 21, 12331 or a NIR to visible or IR to NIR photo-conversion layer such as described, for example, in J. Appl. Phys. 2013, 113, 124509.

Further preferably the OPV or OPD device comprises, between the active layer and the first or second electrode, one or more additional buffer layers acting as hole transporting layer and/or electron blocking layer, which comprise a material such as metal oxides, like for example, ZTO, $MoO_x$, $NiO_x$, a doped conjugated polymer, like for example PEDOT:PSS and polypyrrole-polystyrene sulfonate (PPy:PSS), a conjugated polymer, like for example polytriarylamine (PTAA), an organic compound, like for example substituted triaryl amine derivatives such as N,N'-diphenyl-N,N'-bis(1-naphthyl)(1,1'-biphenyl)-4,4'diamine (NPB), N,N'-diphenyl-N,N'-(3-methylphenyl)-1,1'-biphenyl-4,4'-diamine (TPD), graphene based materials, like for example, graphene oxide and graphene quantum dots or alternatively as hole blocking layer and/or electron transporting layer, which comprise a material such as metal oxide, like for example, $ZnO_x$, $TiO_x$, AZO (aluminium doped zinc oxide), a salt, like for example LiF, NaF, CsF, a conjugated polymer electrolyte, like for example poly[3-(6-trimethylammoniumhexyl) thiophene], poly(9,9-bis(2-ethylhexyl)-fluorene]-b-poly[3-(6-trimethylammoniumhexyl)thiophene], or poly[(9,9-bis (3'-(N,N-dimethylamino)propyl)-2,7-fluorene)-alt-2,7-(9,9-dioctylfluorene)], a polymer, like for example poly (ethyleneimine) or crosslinked N-containing compound derivatives or an organic compound, like for example tris (8-quinolinolato)-aluminium(III) ($Alq_3$), phenanthroline derivative or $C_{60}$ or $C_{70}$ based fullerenes, like for example, as described in *Adv. Energy Mater.* 2012, 2, 82-86.

In a fullerene composition comprising a fullerene mixture and a polymer according to the present invention, the ratio polymer:fullerene mixture is preferably from 5:1 to 1:5 by weight, more preferably from 1:0.5 to 1:3 by weight, most preferably 1:1 to 1:2 by weight. A polymeric binder may also be included, from 5 to 95% by weight. Examples of binder include polystyrene (PS), polypropylene (PP) and polymethylmethacrylate (PMMA).

To produce thin layers in OE devices, like BHJ OPV devices, a fullerene mixture, fullerene composition or formulation according to the present invention may be deposited by any suitable method. Liquid coating of devices is more desirable than vacuum deposition techniques. Solution deposition methods are especially preferred. The formulations of the present invention enable the use of a number of liquid coating techniques. Preferred deposition techniques include, without limitation, dip coating, spin coating, ink jet printing, nozzle printing, letter-press printing, screen printing, gravure printing, doctor blade coating, roller printing, reverse-roller printing, offset lithography printing, dry offset lithography printing, flexographic printing, web printing, spray coating, curtain coating, brush coating, slot dye coating or pad printing. For the fabrication of OPV devices and modules area printing method compatible with flexible substrates are preferred, for example slot dye coating, spray coating and the like.

When preparing a suitable solution or formulation containing a composition with a fullerene mixture (as n-type component) and a polymer (as p-type component) according to the present invention, a suitable solvent should be selected so as to ensure full dissolution of both the p-type and the n-type component, and to take into account the boundary conditions (for example rheological properties) introduced by the chosen printing method.

Organic solvents are generally used for this purpose. Typical solvents can be aromatic solvents, halogenated solvents or chlorinated solvents, including chlorinated aromatic solvents. Preferred solvents are aliphatic hydrocarbons, chlorinated hydrocarbons, aromatic hydrocarbons, ketones, ethers and mixtures thereof. Examples include, but are not limited to dichloromethane, trichloromethane, tetrachloromethane, chlorobenzene, o-dichlorobenzene, 1,2,4-trichlorobenzene, 1,2-dichloroethane, 1,1,1-trichloroethane, 1,1,2,2-tetrachloroethane, 1,8-diiodooctane, 1-chloronaphthalene, 1,8-octane-dithiol, anisole, 2-methylanisole, phenetol, 4-methyl-anisole, 3-methylanisole, 2,6-dimethylanisole, 2,5-di-methylanisole, 2,4-dimethylanisole, 3,5-dimethylanisole, 4-fluoroanisole, 3-fluoro-anisole, 3-trifluoro-methylanisole, 4-fluoro-3-methylanisole, 2-fluoroanisole, toluene, o-xylene, m-xylene, p-xylene, mixture of xylene o-, m-, and p-isomers, 1,2,4-trimethylbenzene, 1,2,3,4-tetra-methyl benzene, pentylbenzene, mesitylene, cumene, cymene, cyclohexylbenzene, diethylbenzene, cyclohexane, 1-methylnaphthalene, 2-methylnaphthalene, 1,2-dimethylnaphthalene, tetraline, decaline, indane, 1-methyl-4-(1-methylethenyl)-cyclohexene (d-Limonene), 6,6-dimethyl-2-methylenebicyclo[3.1.1]heptanes (β-pinene), 2,6-lutidine, 2-fluoro-m-xylene, 3-fluoro-o-xylene, 2-chloro-benzotrifluoride, 2-chloro-6-fluorotoluene, 2,3-dimethylpyrazine, 2-fluorobenzonitrile, 4-fluoroveratrol, 3-fluorobenzo-nitrile, 1-fluoro-3,5-dimethoxy-benzene, 3-fluorobenzo-trifluoride, benzotrifluoride, trifluoromethoxy-benzene, 4-fluorobenzotrifluoride, 3-fluoropyridine, toluene, 2-fluoro-toluene, 2-fluorobenzotrifluoride, 3-fluorotoluene, 4-isopropylbiphenyl, phenyl ether, pyridine, 4-fluorotoluene, 2,5-difluorotoluene, 1-chloro-2,4-difluorobenzene, 2-fluoropyridine, 3-chlorofluoro-benzene, 1-chloro-2,5-difluorobenzene, 4-chlorofluorobenzene, 2-chlorofluorobenzene, methyl benzoate, ethyl benzoate, nitrobenzene, benzaldehyde, benzonitrile, tetrahydrofuran, 1,4-dioxane, 1,3-dioxane, morpholine, acetone, methylethylketone, ethyl acetate, n-butyl acetate, N,N-dimethylaniline, N,N-dimethylformamide, N-methylpyrrolidinone, dimethylacetamide, dimethylsulfoxide and/or mixtures thereof.

Especially preferred are solvents selected from aliphatic or aromatic hydrocarbons, or mixtures thereof, which are non-chlorinated.

Further preferred are solvents selected from non-chlorinated aliphatic or aromatic hydrocarbons, or mixtures thereof, which contain less than 5% of halogenated but non-chlorinated (e.g. fluorinated, brominated or iodinated) aliphatic or aromatic hydrocarbons, like e.g. 1,8-diiodooctane.

Preferred solvents of this type are selected from 1,2,4-trimethylbenzene, 1,2,3,4-tetra-methyl benzene, pentylbenzene, mesitylene, cumene, cymene, cyclohexylbenzene, diethylbenzene, tetralin, decalin, 2,6-lutidine, N,N-dimethylformamide, 2,3-dimethylpyrazine, 2-methylanisole, phenetol, 4-methyl-anisole, 3-methylanisole, 2,5-dimethylanisole, 2,4-dimethylanisole, 3,5-dimethyl-anisole, N,N-dimethylaniline, ethyl benzoate, 1-methylnaphthalene, 2-methylnaphthalene, N-methylpyrrolidinone, dioxane, 4-isopropylbiphenyl, phenyl ether, pyridine, 1,8-octanedithiol, nitrobenzene, 1-chloronaphthalene, p-xylene, m-xylene, o-xylene or mixture of o-, m-, and p-isomers.

The OPV device can be of any OPV device type known from the literature (see e.g. Waldauf et al., *Appl. Phys. Lett.*, 2006, 89, 233517).

A first preferred OPV device according to the invention comprises the following layers (in the sequence from bottom to top):
  optionally a substrate,
  a high work function electrode, preferably comprising a metal oxide, like for example ITO, serving as anode or a conducting grid
  an optional conducting polymer layer or hole transport layer, preferably comprising an organic polymer or polymer blend, for example PEDOT:PSS (poly(3,4-ethylenedioxythiophene): poly(styrene-sulfonate), substituted triaryl amine derivatives, for example, TBD (N,N'-dyphenyl-N—N'-bis(3-methylphenyl)-1,1'biphenyl-4,4'-diamine) or NBD (N,N'-dyphenyl-N—N'-bis(1-napthylphenyl)-1,1'biphenyl-4,4'-diamine),
  a layer, also referred to as "photoactive layer", comprising a p-type and an n-type organic semiconductor, which can exist for example as a p-type/n-type bilayer or as distinct p-type and n-type layers, or as blend or p-type and n-type semiconductor, forming a BHJ,
  optionally a layer having electron transport properties, for example comprising LiF, $TiO_x$, $ZnO_x$, PFN, a poly (ethyleneimine) or crosslinked nitrogen containing compound derivatives or a phenanthroline derivatives
  a low work function electrode, preferably comprising a metal like for example aluminum, serving as cathode,
  wherein at least one of the electrodes, preferably the anode, is at least partially transparent to visible light, and
  wherein the n-type semiconductor is a fullerene mixture according to the present invention.

A second preferred OPV device according to the invention is an inverted OPV device and comprises the following layers (in the sequence from bottom to top):

optionally a substrate,
a high work function metal or metal oxide electrode, comprising for example ITO, serving as cathode, or a conducting grid
a layer having hole blocking properties, preferably comprising a metal oxide like $TiO_x$ or $ZnO_x$, or comprising an organic compound such as polymer like poly(ethyleneimine) or crosslinked nitrogen containing compound derivatives or phenanthroline derivatives,
a photoactive layer comprising a p-type and an n-type organic semiconductor, situated between the electrodes, which can exist for example as a p-type/n-type bilayer or as distinct p-type and n-type layers, or as blend or p-type and n-type semiconductor, forming a BHJ,
an optional conducting polymer layer or hole transport layer, preferably comprising an organic polymer or polymer blend, for example of PEDOT:PSS or substituted triaryl amine derivatives, for example, TBD or NBD,
an electrode comprising a high work function metal like for example silver, serving as anode,
wherein at least one of the electrodes, preferably the cathode, is at least partially transparent to visible light, and
wherein the n-type semiconductor is a fullerene mixture according to the present invention.

In the OPV devices of the present invention the p-type and n-type semiconductor materials are preferably selected from the materials, like the polymer/fullerene systems, as described above When the photoactive layer is deposited on the substrate, it forms a BHJ that phase separates at nanoscale level. For discussion on nanoscale phase separation see Dennler et al, *Proceedings of the IEEE*, 2005, 93 (8), 1429 or Hoppe et al, *Adv. Func. Mater,* 2004, 14(10), 1005. An optional annealing step may be then necessary to optimize blend morphology and consequently OPV device performance.

Another method to optimize device performance is to prepare formulations for the fabrication of OPV (BHJ) devices that may include additives with variable boiling points to promote phase separation in the right way. 1,8-Octanedithiol, 1,8-diiodooctane, nitrobenzene, 1-chloronaphthalene, N,N-dimethylformamide, dimethylacetamide, dimethylsulfoxide and other additives have been used to obtain high-efficiency solar cells. Examples are disclosed in J. Peet, et al, *Nat. Mater.,* 2007, 6, 497 or Fréchet et al. *J. Am. Chem. Soc.,* 2010, 132, 7595-7597.

As further illustrated in the non-limiting working examples, photovoltaic devices can be prepared which have a power conversion efficiency (PCE) of, for example, at least 2.5%, or at least 3.0%, or at least 4.0%, or at least 5.0%. While there is no particular upper limit on the PCE, the PCE can be, for example, less than 20%, or less than 15%, or less than 10%.

Another preferred embodiment of the present invention relates to the use of a fullerene mixture or fullerene composition according to the present invention as dye, hole transport layer, hole blocking layer, electron transport layer and/or electron blocking layer in a DSSC or a perovskite-based solar cells, and to a DSSC or perovskite-based solar cells comprising a mixture or composition according to the present invention.

DSSCs and perovskite-based solar cells can be manufactured as described in the literature, for example in Chem. Rev. 2010, 110, 6595-6663, Angew. Chem. Int. Ed. 2014, 53, 2-15 or in WO2013171520A1.

The fullerene mixture and fullerene compositions of the present invention can also be used as dye or pigment in other applications, for example as an ink dye, laser dye, fluorescent marker, solvent dye, food dye, contrast dye or pigment in coloring paints, inks, plastics, fabrics, cosmetics, food and other materials.

The fullerene mixture, fullerene compositions and semiconducting layers of the present invention are also suitable for use as n-type semiconductor in other OE devices or device components, for example in the semiconducting channel of an OFET device, or in the buffer layer, electron transport layer (ETL) or hole blocking layer (HBL) of an OLED or OPV device.

Accordingly, the invention also provides an OFET comprising a gate electrode, an insulating (or gate insulator) layer, a source electrode, a drain electrode and an organic semiconducting channel connecting the source and drain electrodes, wherein the organic semiconducting channel comprises a fullerene mixture according to the present invention, a fullerene composition or an organic semiconducting layer according to the present invention as n-type semiconductor. Other features of the OFET are well known to those skilled in the art.

OFETs where an OSC material is arranged as a thin film between a gate dielectric and a drain and a source electrode, are generally known, and are described for example in U.S. Pat. No. 5,892,244, 5,998,804, 6,723,394 and in the references cited in the background section. Due to the advantages, like low cost production using the solubility properties of the compounds according to the invention and thus the processibility of large surfaces, preferred applications of these FETs are such as integrated circuitry, TFT displays and security applications.

The gate, source and drain electrodes and the insulating and semiconducting layer in the OFET device may be arranged in any sequence, provided that the source and drain electrode are separated from the gate electrode by the insulating layer, the gate electrode and the semiconductor layer both contact the insulating layer, and the source electrode and the drain electrode both contact the semiconducting layer.

An OFET device according to the present invention preferably comprises:
a source electrode,
a drain electrode,
a gate electrode,
a semiconducting layer,
one or more gate insulator layers,
optionally a substrate.
wherein the semiconductor layer comprises a fullerene mixture or a fullerene composition according to the present invention.

The OFET device can be a top gate device or a bottom gate device. Suitable structures and manufacturing methods of an OFET device are known to the skilled in the art and are described in the literature, for example in US 2007/0102696 A1.

The gate insulator layer preferably comprises a fluoropolymer, like e.g. the commercially available Cytop 809M® or Cytop 107M® (from Asahi Glass). Preferably the gate insulator layer is deposited, e.g. by spin-coating, doctor blading, wire bar coating, spray or dip coating or other known methods, from a formulation comprising an insulator material and one or more solvents with one or more fluoro atoms (fluorosolvents), preferably a perfluorosolvent. A suitable perfluorosolvent is e.g. FC75® (available from Acros, catalogue number 12380). Other suitable fluoropolymers and fluorosolvents are known in prior art, like for example the perfluoropolymers Teflon AF® 1600 or 2400 (from DuPont) or Fluoropel® (from Cytonix) or the perfluorosolvent FC 43® (Acros, No. 12377). Especially preferred are organic dielectric materials having a low permittivity (or dielectric constant) from 1.0 to 5.0, very preferably from 1.8 to 4.0 ("low k materials"), as disclosed for example in US 2007/0102696 A1 or U.S. Pat. No. 7,095,044.

In security applications, OFETs and other devices with semiconducting materials according to the present invention, like transistors or diodes, can be used for RFID tags or security markings to authenticate and prevent counterfeiting of documents of value like banknotes, credit cards or ID cards, national ID documents, licenses or any product with monetry value, like stamps, tickets, shares, cheques etc.

Alternatively, the fullerene mixtures, fullerene compositions, and semiconducting layers according to the invention can be used in OLEDs, for example in the buffer layer, ETL or HBL of an OLED. The OLED device can be used for example as the active display layer in a flat panel display device, or as the backlight of a flat panel display like for example a liquid crystal display. Common OLEDs are realized using multilayer structures. An emission layer is generally sandwiched between one or more electron-transport and/or hole-transport layers. By applying an electric voltage electrons and holes as charge carriers move towards the emission layer where their recombination leads to the excitation and hence luminescence of the lumophor units contained in the emission layer.

The fullerene mixture, fullerene composition or semiconducting layer according to the present invention may be employed in one or more of the ETL, HBL or buffer layer, especially their water-soluble derivatives (for example with polar or ionic side groups) or ionically doped forms. The processing of such layers, comprising a semiconductor material of the present invention, for the use in OLEDs is generally known by a person skilled in the art, see, e.g., Müller et al, *Synth. Metals,* 2000, 111-112, 31-34, Alcala, *J. Appl. Phys.,* 2000, 88, 7124-7128, O'Malley et al, *Adv. Energy Mater.* 2012, 2, 82-86 and the literature cited therein.

According to another use, the fullerene mixtures, fullerene compositions, and materials according to this invention, especially those showing photoluminescent properties, may be employed as materials of light sources, e.g. in display devices, as described in EP 0 889 350 A1 or by C. Weder et al., *Science,* 1998, 279, 835-837.

A further aspect of the invention relates to both the oxidised and reduced form of a fullerene mixture according to this invention. Either loss or gain of electrons results in formation of a highly delocalised ionic form, which is of high conductivity. This can occur on exposure to common dopants. Suitable dopants and methods of doping are known to those skilled in the art, e.g. from EP 0 528 662, U.S. Pat. No. 5,198,153 or WO 96/21659.

The doping process typically implies treatment of the semiconductor material with an oxidating or reducing agent in a redox reaction to form delocalised ionic centres in the material, with the corresponding counterions derived from the applied dopants. Suitable doping methods comprise for example exposure to a doping vapor in the atmospheric pressure or at a reduced pressure, electrochemical doping in a solution containing a dopant, bringing a dopant into contact with the semiconductor material to be thermally diffused, and ion-implantantion of the dopant into the semiconductor material.

When electrons are used as carriers, suitable dopants are for example halogens (e.g., $I_2$, $Cl_2$, $Br_2$, ICl, $ICl_3$, IBr and IF), Lewis acids (e.g., $PF_5$, $AsF_5$, $SbF_5$, $BF_3$, $BCl_3$, $SbCl_5$, $BBr_3$ and $SO_3$), protonic acids, organic acids, or amino acids (e.g., HF, HCl, $HNO_3$, $H_2SO_4$, $HClO_4$, $FSO_3H$ and $ClSO_3H$), transition metal compounds (e.g., $FeCl_3$, FeOCl, $Fe(ClO_4)_3$, $Fe(4-CH_3C_6H_4SO_3)_3$, $TiCl_4$, $ZrCl_4$, $HfCl_4$, $NbF_5$, $NbCl_5$, $TaCl_5$, $MoF_5$, $MoCl_5$, $WF_5$, $WCl_6$, $UF_6$ and $LnCl_3$ (wherein Ln is a lanthanoid), anions (e.g., $Cl^-$, $Br^-$, $I^-$, $I_3^-$, $HSO_4^-$, $SO_4^{2-}$, $NO_3^-$, $ClO_4^-$, $BF_4^-$, $PF_6^-$, $AsF_6^-$, $SbF_6^-$, $FeCl_4^-$, $Fe(CN)_6^{3-}$, and anions of various sulfonic acids, such as aryl-$SO_3^-$). When holes are used as carriers, examples of dopants are cations (e.g., $H^+$, $Li^+$, $Na^+$, $K^+$, $Rb^+$ and $Cs^+$), alkali metals (e.g., Li, Na, K, Rb, and Cs), alkaline-earth metals (e.g., Ca, Sr, and Ba), $O_2$, $XeOF_4$, $(NO_2^+)(SbF_6^-)$, $(NO_2^+)(SbCl_6^-)$, $(NO_2^+)(BF_4^-)$, $AgClO_4$, $H_2IrCl_6$, $La(NO_3)_3 \cdot 6H_2O$, $FSO_2OOSO_2F$, Eu, acetylcholine, $R_4N^+$, (R is an alkyl group), $R_4P^+$ (R is an alkyl group), $R_6As^+$ (R is an alkyl group), and $R_3S^+$ (R is an alkyl group).

The conducting form of a fullerene mixture of the present invention can be used as an organic "metal" in applications including, but not limited to, charge injection layers and ITO planarising layers in OLED applications, films for flat panel displays and touch screens, antistatic films, printed conductive substrates, patterns or tracts in electronic applications such as printed circuit boards and condensers.

According to another use, the fullerene mixtures and fullerene compositions according to the present invention can be used alone or together with other materials in or as alignment layers in LCD or OLED devices, as described for example in US 2003/0021913. The use of charge transport compounds according to the present invention can increase the electrical conductivity of the alignment layer. When used in an LCD, this increased electrical conductivity can reduce adverse residual dc effects in the switchable LCD cell and suppress image sticking or, for example in ferroelectric LCDs, reduce the residual charge produced by the switching of the spontaneous polarisation charge of the ferroelectric LCs.

When used in an OLED device comprising a light emitting material provided onto the alignment layer, this increased electrical conductivity can enhance the electroluminescence of the light emitting material. The fullerene mixtures, fullerene compositions, and materials according to the present invention may also be combined with photoisomerisable compounds and/or chromophores for use in or as photoalignment layers, as described in US 2003/0021913 A1.

According to another use the fullerene mixtures, fullerene compositions, and materials according to the present invention, especially their water-soluble derivatives (for example with polar or ionic side groups) or ionically doped forms, can be employed as chemical sensors or materials for detecting and discriminating DNA sequences. Such uses are described for example in L. Chen, D. W. McBranch, H. Wang, R. Helgeson, F. Wudl and D. G. Whitten, *Proc. Natl. Acad. Sci. U.S.A.,* 1999, 96, 12287; D. Wang, X. Gong, P. S. Heeger, F. Rininsland, G. C. Bazan and A. J. Heeger, *Proc. Natl. Acad. Sci. U.S.A.,* 2002, 99, 49; N. DiCesare, M. R. Pinot, K. S. Schanze and J. R. Lakowicz, *Langmuir,* 2002, 18, 7785; D. T. McQuade, A. E. Pullen, T. M. Swager, *Chem. Rev.,* 2000, 100, 2537.

Unless the context clearly indicates otherwise, as used herein plural forms of the terms herein are to be construed as including the singular form and vice versa.

Throughout the description and claims of this specification, the words "comprise" and "contain" and variations of the words, for example "comprising" and "comprises", mean "including but not limited to", and are not intended to (and do not) exclude other components.

It will be appreciated that variations to the foregoing embodiments of the invention can be made while still falling within the scope of the invention. Each feature disclosed in this specification, unless stated otherwise, may be replaced by alternative features serving the same, equivalent or similar purpose. Thus, unless stated otherwise, each feature disclosed is one example only of a generic series of equivalent or similar features.

All of the features disclosed in this specification may be combined in any combination, except combinations where at least some of such features and/or steps are mutually exclusive. In particular, the preferred features of the invention are applicable to all aspects of the invention and may be used in any combination. Likewise, features described in non-essential combinations may be used separately (not in combination).

Above and below, unless stated otherwise percentages are percent by weight and temperatures are given in ° C. The values of the dielectric constant E ("permittivity") refer to values taken at 20° C. and 1,000 Hz.

The invention will now be described in more detail by reference to the following examples, which are illustrative only and do not limit the scope of the invention.

Example 1

Bulk Heterojunction Organic Photovoltaic Devices for Fullerene Mixtures

Organic photovoltaic (OPV) devices are fabricated on pre-patterned ITO-glass substrates (13 Ω/sq.) purchased from LUMTEC Corporation. Substrates are cleaned using common solvents (acetone, iso-propanol, deionized-water) in an ultrasonic bath. A layer of commercially available PVE-002 (Merck) was applied as a uniform coating by doctor blade at 80° C. The PVE-002 Films are then annealed at 100° C. for 10 minutes in air and then transferred into a Nitrogen atmosphere. Active material solutions (i.e. polymer+fullerene) are prepared to fully dissolve the solutes at a 30 mg·cm$^{-3}$ solution concentration in 1-methylnaphthalene (1 MN) or 2,4-dimethylanisole (DMA). Thin films are blade-coated in a nitrogen atmosphere to achieve active layer thicknesses between 50 and 800 nm as measured using a profilometer. A short drying period follows to ensure removal of any residual solvent.

Typically, blade-coated films are dried at 90° C. for 2 minutes on a hotplate. Next the devices are transferred into an air atmosphere. On top of the active layer 0.9 mL of a conducting polymer poly(ethylene dioxythiophene) doped with poly(styrene sulfonic acid) [PEDOT:PSS Clevios HTL Solar SCA 246-10 (Heraeus)] was spread and uniformly coated by spin-coating at 1100 rpm for 130 seconds. Afterwards Ag (100 nm) cathodes are thermally evaporated through a shadow mask to define the cells. For the last step of the device fabrication, the devices were each encapsulated with a glass cover slide using UV-curing epoxy glue.

Current-voltage characteristics are measured using a Keithley 2400 SMU while the solar cells are illuminated by a Newport Solar Simulator at 100 mW·cm$^{-2}$ white light. The solar simulator is equipped with AM1.5G filters. The illumination intensity is calibrated using a Si photodiode. All the device preparation and characterization is done in a dry-nitrogen atmosphere.

Power conversion efficiency is calculated using the following expression $$\eta = \frac{V_{oc} \times J_{sc} \times FF}{P_{in}}$$

where FF is defined as $$FF = \frac{V_{max} \times J_{max}}{V_{oc} \times J_{sc}}$$

OPV device characteristics for a blend of Polymer 1 having the structure shown below and fullerene coated from an organic solution at a total solid concentration are shown in Table 1. Polymer 1 and its preparation are disclosed in WO 2011/131280 A1.

Polymer 1

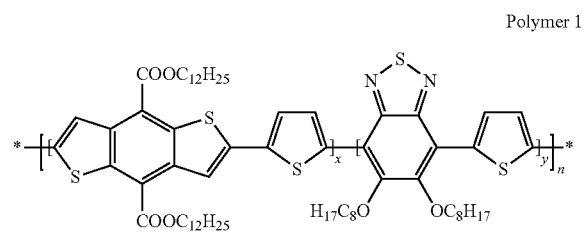

Table 1 shows the formulation characteristics of the individual photoactive material solutions comprising a polymer as electron donor component and a fullerene mixture as electron acceptor component. Solutions C1, C2 and C3 according to prior art contain fullerene PCBM-C60, a mixture of PCBM-C60 with the corresponding bisadduct BisP-CBM-C60, or a mixture of PCBM-C60 and PCBM-C70, respectively. Solutions 1, 2 and 3 according to the present invention contain a mixture of fullerenes PCBM-C60 and PCBC$_6$-C60, which differ in the nature of their ester substituent (methyl ester vs. hexyl ester), at different concentrations. The polymer is in all cases Polymer 1. The solvent is in all cases 1-methylnaphthalene.

TABLE 1

| Formulation characteristics | | | | |
|---|---|---|---|---|
| No. | Fullerene 1 | Fullerene 2 | Ratio Polymer 1:Fullerene 1:Fullerene 2 | Solvent |
| C1 | PCBM-C60 | — | 1.00:2:00 | 1MN |
| C2 | PCBM-C60 | BisPCBM-C60 | 1.00:1.84:0.16 | 1MN |
| C3 | PCBM-C60 | PCBM-C70 | 1.00:1.62:0.38 | 1MN |
| 1 | PCBM-C60 | PCBC$_6$-C60 | 1.00:1.60:0.40 | 1MN |
| 2 | PCBM-C60 | PCBC$_6$-C60 | 1.00:1.34:0.66 | 1MN |
| 3 | PCBM-C60 | PCBC$_6$-C60 | 1.00:0.66:1.34 | 1MN |

Initial Device Properties

Table 2 shows the device characteristics for the individual OPV devices comprising an photoactive layer with a BHJ formed from the active material (fullerene mixture/polymer) solutions of Table 1.

TABLE 2

Photovoltaic cell characteristics after continuous simulated solar irradiation (AM1.5G)

| No. | <1 Day Max Performance | | | | After 9 Days | | | |
|---|---|---|---|---|---|---|---|---|
| | Voc mV | Jsc mA·cm$^{-2}$ | FF % | PCE % | Voc mV | Jsc mA·cm$^{-2}$ | FF % | PCE % |
| C1 | 740 | 13.3 | 47.7 | 4.70 | 757 | 10.9 | 45.2 | 3.73 |
| C2 | 747 | 13.0 | 50.9 | 4.93 | 760 | 10.9 | 46.6 | 3.86 |
| C3† | 715 | 13.4 | 39.1 | 3.74 | 715 | 10.3 | 45.3 | 3.33 |
| 1 | 749 | 14.7 | 46.0 | 5.07 | 768 | 11.3 | 44.4 | 3.85 |
| 2 | 760 | 14.5 | 50.1 | 5.52 | 780 | 11.1 | 45.2 | 3.95 |
| 3 | 790 | 14.6 | 50.0 | 5.78 | 783 | 12.7 | 46.6 | 4.64 |

†Performance still evolving due to low PCE starting point

From Table 2 it can be seen that OPV devices with a BHJ prepared from solution 1, 2 or 3 according to the invention, comprising a mixture of two fullerenes PCBM-C60 and PCBC$_6$-C60 with different substituents R, show a higher PCE when deposited from a non-chlorinated solvent, and maintaining the higher PCE even after 9 days of AM1.5G simulated solar irradiation.

Compared thereto, OPV devices with a BHJ prepared from solution C1 with pure PCBM-C60, solution C2 with PCBM-C60 and 8% BisPCBM-C60, and solution C3 with PCBM-C60 and 19% PCBM-C70, as disclosed in or suggested by prior art, show lower values of the PCE. Especially OPV devices with a BHJ prepared from solution C3 (PCBM-C60 with 19% PCBM-C70), showed significantly lower starting PCEs than the active material solutions according to the present invention.

Example 2

BHJ OPV devices were prepared as described in Example 1 from Polymer 1 and further fullerene mixtures according to the invention. For comparison purpose reference BHJ devices were prepared using a single fullerene.

Table 3 shows the formulation characteristics of the individual photoactive material solutions, comprising Polymer 1 as electron donor component and a fullerene or fullerene mixture as electron acceptor component. Solutions C4 and C5 are reference devices comparing the performance of pure fullerenes of formula I1d or I6b respectively. Solutions 4, 5, 6 and 7 according to the present invention contain a mixture of fullerenes PCBM-C60, PCBC$_6$-C60, formula I1d, formula I6a and formula I6b (wherein R$^{11}$=C$_7$H$_{15}$), which differ in the nature of their ester substituent (methyl ester vs. hexyl ester), the nature of their phenyl substituent (phenyl vs. tetramethoxyphenyl), the nature of their alkyl substituent (R$^{11}$=H vs. R$^{11}$=C$_7$H$_{15}$) and the nature of their adduct type (formula I1 vs. formula I6). The solvent is 1-methylnaphthalene (1 MN) or 2,4-dimethylanisole (DMA).

TABLE 3

Formulation characteristics

| No. | Fullerene 1 | Fullerene 2 | Ratio Polymer 1:Fullerene 1:Fullerene 2 | Solvent |
|---|---|---|---|---|
| C4 | I1d | — | 1.00:2:00 | 1MN |
| 4 | I1d | PCBM-C60 | 1.00:1.00:1.00 | 1MN |
| C5 | I6b (R$^{11}$ = C$_7$H$_{15}$) | — | 1.00:2.00 | DMA |
| 5 | I6b (R$^{11}$ = C$_7$H$_{15}$) | I6a | 1.00:1.00:1.00 | DMA |

TABLE 3-continued

Formulation characteristics

| No. | Fullerene 1 | Fullerene 2 | Ratio Polymer 1:Fullerene 1:Fullerene 2 | Solvent |
|---|---|---|---|---|
| 6 | I6b (R$^{11}$ = C$_7$H$_{15}$) | PCBC$_6$-C60 | 1.00:1.00:1.00 | 1MN |
| 7 | I6b (R$^{11}$ = C$_7$H$_{15}$) | PCBM-C60 | 1.00:1.00:1.00 | 1MN |

Initial Device Properties

Table 4 shows the device characteristics for the individual OPV devices comprising an photoactive layer with a BHJ formed from the active material (fullerene mixture/polymer) solutions of Table 1.

TABLE 4

Photovoltaic cell characteristics after continuous simulated solar irradiation (AM1.5G)

| No. | Performance initial PCE % | Performance after 100 hours PCE % |
|---|---|---|
| C4 | 4.94 | 2.96 |
| 4 | 6.24 | 4.40 |
| C5 | 3.49 | 3.27 |
| 5 | 5.39 | 4.48 |
| 6 | 3.63 | 3.27 |
| 7 | 5.26 | 3.60 |

From Table 4 it can be seen that OPV devices with a BHJ prepared from solution 4, 5, 6 or 7, according to the invention comprising a mixture of two fullerenes PCBM-C60, PCBC$_6$-C60, I1d, I6a or I6b (wherein R$^{11}$=C$_7$H$_{15}$) with different substituents show a higher PCE when deposited from a non-chlorinated solvent, and maintaining higher PCE beyond 100 hours of AM1.5G simulated solar irradiation.

Compared thereto, OPV devices with a BHJ prepared from solution D4 with pure fullerene I1d, solution D5 with pure fullerene I6b (R$^{11}$=C$_7$H$_{15}$), as disclosed in or suggested by prior art, show lower values of the PCE.

The invention claimed is:

1. A mixture comprising
a first compound of formula I1

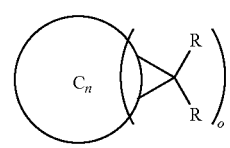

I1 wherein C$_n$ is a fullerene in which n=60,
o is 1 or 2, one substituent R is benzene, and the other substituent R is an ester group of formula C-34

C-34 wherein a is 3, and R$^{11}$ is methyl, and
a second compound of formula I1, wherein o is 1 or 2, one substituent R is benzene, and the other substituent R is an ester group of formula C-34, wherein a is 3 and $R^{11}$ is ethyl, propyl, butyl, pentyl or hexyl.

2. The mixture according to claim 1, wherein at least one compound of formula I1 is

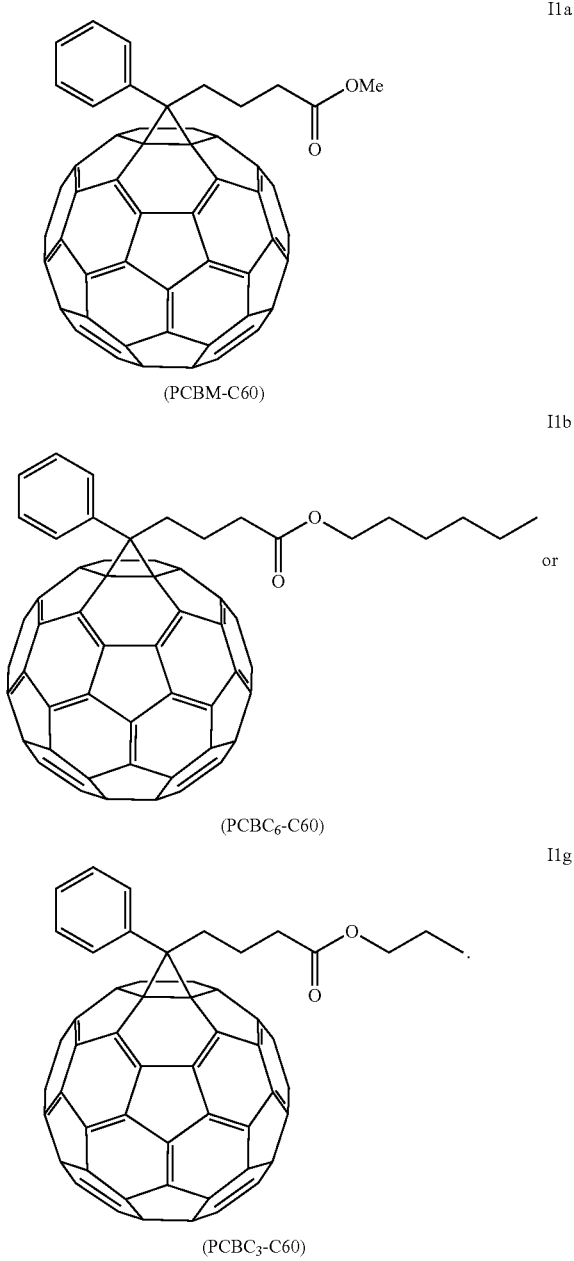

(PCBM-C60)   I1a (PCBC$_6$-C60)   I1b or (PCBC$_3$-C60)   I1g

3. The mixture according to claim 2, comprising a compound of formula I1a and a compound of formula I1.

4. A semiconducting material, organic electronic device or component of an organic electronic device comprising an electron acceptor or n-type semiconductor that is the mixture of claim 1.

5. A composition comprising the mixture according to claim 1 as electron acceptor or n-type semiconductor component, and further comprising one or more semiconducting compounds which have electron donor or p-type properties.

6. The composition according to claim 5, wherein the semiconducting compounds which have electron donor or p-type properties are selected from conjugated organic polymers.

7. The composition comprising a mixture according claim 1 and one or more compounds which are selected from compounds having one or more of a semiconducting, charge transport, hole transport, electron transport, hole blocking, electron blocking, electrically conducting, photoconducting, photoactive and light emitting property.

8. A semiconducting, charge transport, electrically conducting, photoconducting, photoactive thermoelectric material, light emitting material, an organic electronic (OE) device, a component of an OE device or an assembly comprising an OE device containing the mixture of claim 1.

9. A semiconducting, charge transport, electrically conducting, photoconducting, photoactive, thermoelectric or light emitting material, which comprises the mixture according to claim 1.

10. A mixture according to claim 1 further comprising one or more organic solvents.

11. An OE device, or a component thereof, or an assembly comprising it, which is prepared using the mixture of claim 10.

12. An OE device, or a component thereof, or an assembly comprising it, comprising the mixture according to claim 1.

13. The OE device according to claim 11, which is an optical, electrooptical, electronic, electroluminescent, photoluminescent, photoactive or thermoelectric device.

14. The OE device according to claim 11, which is selected from organic field effect transistors (OFET), organic thin film transistors (OTFT), organic light emitting diodes (OLED), organic light emitting transistors (OLET), organic photovoltaic devices (OPV), organic photodetectors (OPD), organic solar cells, dye sensitized solar cells (DSSC), thermoelectric devices, laser diodes, Schottky diodes, photoconductors and photodetectors.

15. The component of claim 12, which is selected from charge injection layers, charge transport layers, interlayers, planarising layers, antistatic films, polymer electrolyte membranes (PEM), conducting substrates and conducting patterns.

16. The assembly of claim 12, which is selected from integrated circuits (IC), radio frequency identification (RFID) tags or security markings or security devices containing them, flat panel displays or backlights thereof, electrophotographic devices, electrophotographic recording devices, organic memory devices, sensor devices, biosensors and biochips.

17. The OE device according to claim 14, which is a bulk heterojunction (BHJ) OPV device or an inverted BHJ OPV device.

18. A bulk heterojunction comprising, or being formed from, the composition of claim 5.

19. The mixture according to claim 1, wherein in the second compound of formula I1 $R^{11}$ is hexyl.

20. The mixture according to claim 1, which further comprises a compound of formula I1'

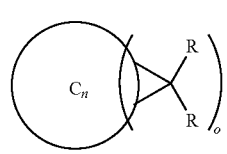

I1' wherein $C_n$ is C70, o is 1 or 2, one substituent R is benzene and the other substituent R is an ester group of formula C-34, in which a is 3 and $R^{11}$ is methyl, ethyl, propyl, butyl, pentyl or hexyl.

* * * * *